(12) United States Patent
Jervis et al.

(10) Patent No.: US 7,875,056 B2
(45) Date of Patent: Jan. 25, 2011

(54) WEDGE OPERATED RETAINER DEVICE AND METHODS

(75) Inventors: James E. Jervis, Atherton, CA (US); John Ashley, San Francisco, CA (US)

(73) Assignee: Anpa Medical, Inc., San Mateo, CA (US)

( * ) Notice: Subject to any disclaimer, the term of this patent is extended or adjusted under 35 U.S.C. 154(b) by 1275 days.

(21) Appl. No.: 11/380,573

(22) Filed: Apr. 27, 2006

(65) Prior Publication Data

US 2007/0021781 A1    Jan. 25, 2007

Related U.S. Application Data

(60) Provisional application No. 60/701,629, filed on Jul. 22, 2005.

(51) Int. Cl.
*A61B 17/04* (2006.01)

(52) U.S. Cl. .................. 606/232; 24/136 R; 24/115 M

(58) Field of Classification Search ............... 606/232, 606/72, 139, 142; 24/136 R, 115 M
See application file for complete search history.

(56) References Cited

U.S. PATENT DOCUMENTS

| | | | |
|---|---|---|---|
| 523,273 A * | 7/1894 | Fouts ........................ 104/222 |
| 2,040,678 A * | 5/1936 | Van Buskirk ............... 403/303 |
| 2,828,147 A * | 3/1958 | Peiffer ........................ 285/421 |
| 3,498,575 A | 3/1970 | Downing |
| 3,758,922 A * | 9/1973 | Field ........................ 24/136 R |
| 3,776,586 A * | 12/1973 | Ahlgren et al. ......... 294/102.1 |
| 3,778,868 A * | 12/1973 | Kelly ........................ 403/361 |
| 3,868,748 A * | 3/1975 | Kelly ........................ 24/115 M |
| 3,974,621 A * | 8/1976 | Stang ........................... 411/75 |
| 4,002,822 A * | 1/1977 | Kurosaki ................. 174/153 G |
| 4,262,409 A * | 4/1981 | Madej ..................... 29/525.03 |
| 4,811,735 A | 3/1989 | Nash et al. |
| 4,901,721 A * | 2/1990 | Hakki ........................ 606/103 |
| 4,969,892 A | 11/1990 | Burton et al. |
| 5,015,023 A * | 5/1991 | Hall ........................ 294/102.1 |
| 5,026,363 A | 6/1991 | Pratt |
| 5,123,914 A | 6/1992 | Cope |
| 5,156,610 A | 10/1992 | Reger |
| 5,190,561 A | 3/1993 | Graber |
| 5,197,166 A * | 3/1993 | Meier et al. ............... 24/115 G |

(Continued)

OTHER PUBLICATIONS

James E. Jervis, U.S. Appl. No. 11/061,128, entitled "Suture retainer with multiple circumferentially spaced attachment points and suture retention method," filed Feb. 17, 2005.

(Continued)

*Primary Examiner*—Darwin P Erezo
*Assistant Examiner*—Mark Mashack
(74) *Attorney, Agent, or Firm*—Ryan Kromholz & Manion, S.C.

(57) ABSTRACT

This invention relates generally to retainers and methods of using retainers. In particular, the invention relates to a suture retainer adapted for application on a subject by use of an introducing device, such as a catheter. The suture retainer comprises two elements, such as wedge-shaped or substantially wedge-shaped elements, that are positioned such that the elements are juxtaposed with respect to each other. In operation the two elements are engaged by a spring which forces the two elements into contact. Additionally, a housing can be provided.

14 Claims, 31 Drawing Sheets

U.S. PATENT DOCUMENTS

| | | | |
|---|---|---|---|
| 5,211,651 A | 5/1993 | Reger et al. | |
| 5,234,449 A | 8/1993 | Bruker et al. | |
| 5,324,308 A * | 6/1994 | Pierce | 606/232 |
| 5,369,849 A * | 12/1994 | De France | 24/136 R |
| 5,383,905 A * | 1/1995 | Golds et al. | 606/232 |
| 5,391,173 A | 2/1995 | Wilk | |
| 5,405,359 A * | 4/1995 | Pierce | 606/232 |
| 5,413,585 A | 5/1995 | Pagedas | |
| 5,441,224 A | 8/1995 | Ludwig | |
| 5,626,590 A | 5/1997 | Wilk | |
| 5,643,295 A | 7/1997 | Yoon | |
| 5,643,297 A | 7/1997 | Nordgren et al. | |
| 5,643,298 A | 7/1997 | Nordgren et al. | |
| 5,645,553 A | 7/1997 | Kolesa et al. | |
| 5,702,397 A * | 12/1997 | Goble et al. | 606/232 |
| 5,735,877 A | 4/1998 | Pagedas | |
| 5,737,808 A * | 4/1998 | Ikeda | 24/115 G |
| 5,741,301 A | 4/1998 | Pagedas | |
| 5,810,853 A | 9/1998 | Yoon | |
| 5,845,645 A | 12/1998 | Bonutti | |
| 5,895,393 A | 4/1999 | Pagedas | |
| 5,902,321 A * | 5/1999 | Caspari et al. | 606/232 |
| 5,948,001 A | 9/1999 | Larsen | |
| 5,957,903 A | 9/1999 | Mirzaee et al. | |
| 6,015,428 A | 1/2000 | Pagedas | |
| 6,039,176 A | 3/2000 | Wright | |
| 6,066,160 A * | 5/2000 | Colvin et al. | 606/232 |
| 6,077,292 A * | 6/2000 | Bonutti | 606/232 |
| 6,086,608 A * | 7/2000 | Ek et al. | 606/232 |
| 6,231,592 B1 | 5/2001 | Bonutti et al. | |
| 6,432,123 B2 | 8/2002 | Schwartz et al. | |
| 6,475,229 B1 | 11/2002 | Pagedas | |
| 6,699,263 B2 | 3/2004 | Cope | |
| 6,736,847 B2 * | 5/2004 | Seyr et al. | 623/13.14 |
| 6,770,076 B2 * | 8/2004 | Foerster | 606/326 |
| 6,780,187 B2 * | 8/2004 | Supinski | 623/13.14 |
| 6,896,686 B2 | 5/2005 | Webber | |
| 6,902,545 B2 | 6/2005 | Bertolero et al. | |
| 6,984,241 B2 * | 1/2006 | Lubbers et al. | 606/232 |
| 6,997,189 B2 * | 2/2006 | Biggs et al. | 128/898 |
| 7,108,710 B2 * | 9/2006 | Anderson | 606/232 |
| 7,708,759 B2 * | 5/2010 | Lubbers et al. | 606/232 |
| 2001/0051816 A1 * | 12/2001 | Enzerink et al. | 606/232 |
| 2002/0111653 A1 * | 8/2002 | Foerster | 606/232 |
| 2003/0115723 A1 * | 6/2003 | Shuey | 24/136 R |
| 2003/0153922 A1 * | 8/2003 | Supinski | 606/72 |
| 2003/0195562 A1 | 10/2003 | Collier et al. | |
| 2004/0024420 A1 * | 2/2004 | Lubbers et al. | 606/232 |
| 2004/0044366 A1 | 3/2004 | Bonutti et al. | |
| 2004/0078054 A1 * | 4/2004 | Biggs et al. | 606/232 |
| 2004/0098050 A1 * | 5/2004 | Foerster et al. | 606/232 |
| 2004/0102809 A1 * | 5/2004 | Anderson | 606/232 |
| 2004/0220617 A1 * | 11/2004 | Pedlick et al. | 606/232 |
| 2004/0260344 A1 | 12/2004 | Lyons et al. | |
| 2004/0260345 A1 * | 12/2004 | Foerster | 606/232 |
| 2006/0265012 A1 * | 11/2006 | Anderson | 606/232 |
| 2008/0082130 A1 * | 4/2008 | Ward | 606/232 |

OTHER PUBLICATIONS

James E. Jervis, U.S. Appl. No. 11/061,320, entitled "Suture retainer with suture guide and method of using a suture retainer with a suture guide," filed Feb. 17, 2005.

James E. Jervis, et al. U.S. Appl. No. 11/249,008, entitled "Helical retainer, tool for using the helical retainer, and methods," filed Oct. 11, 2005.

* cited by examiner

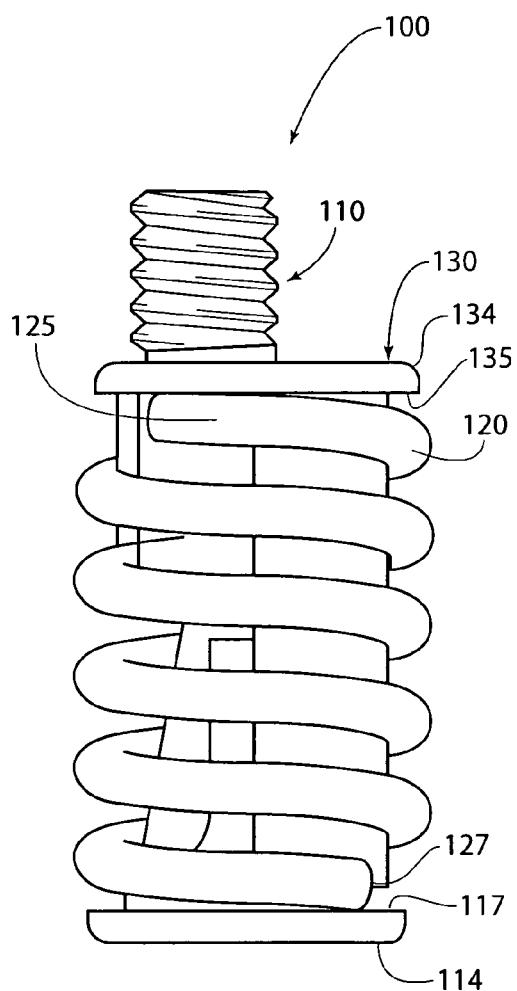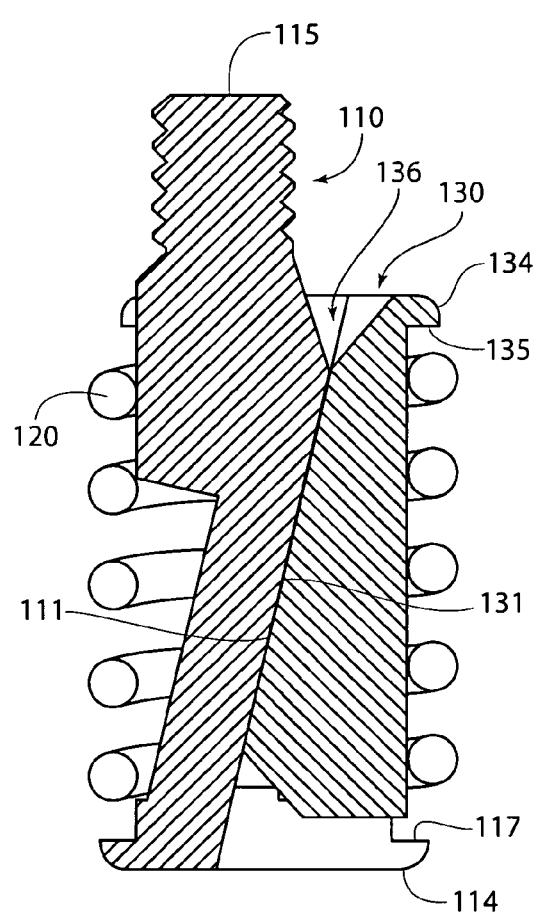
Fig. 9A
Fig. 9B

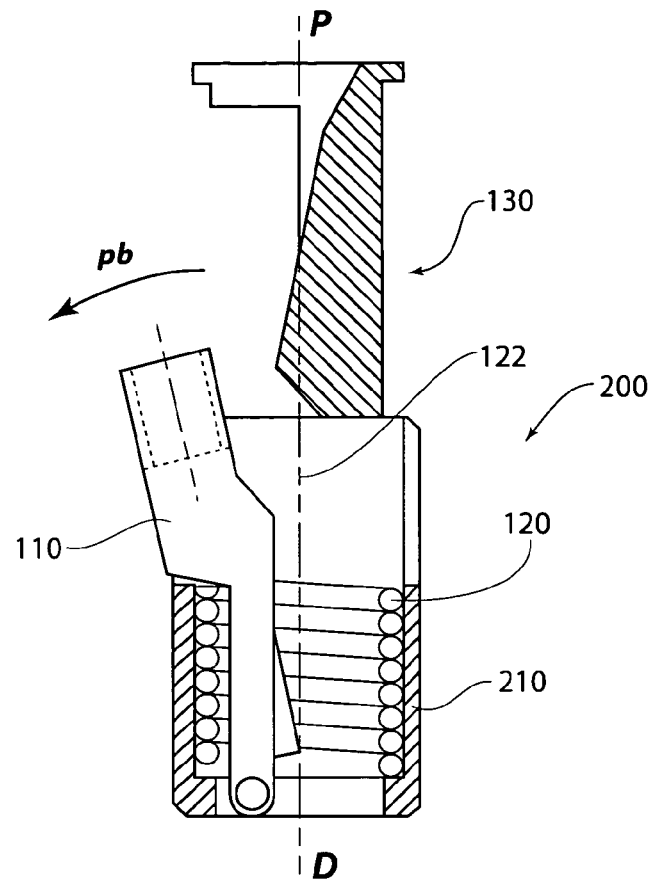
Fig. 10A
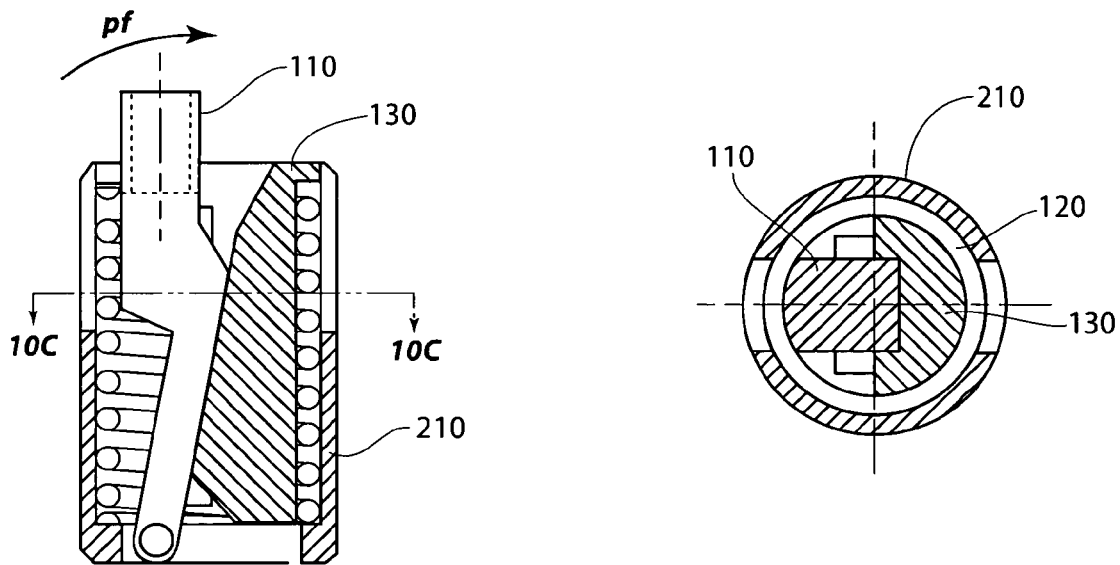
Fig. 10B
Fig. 10C

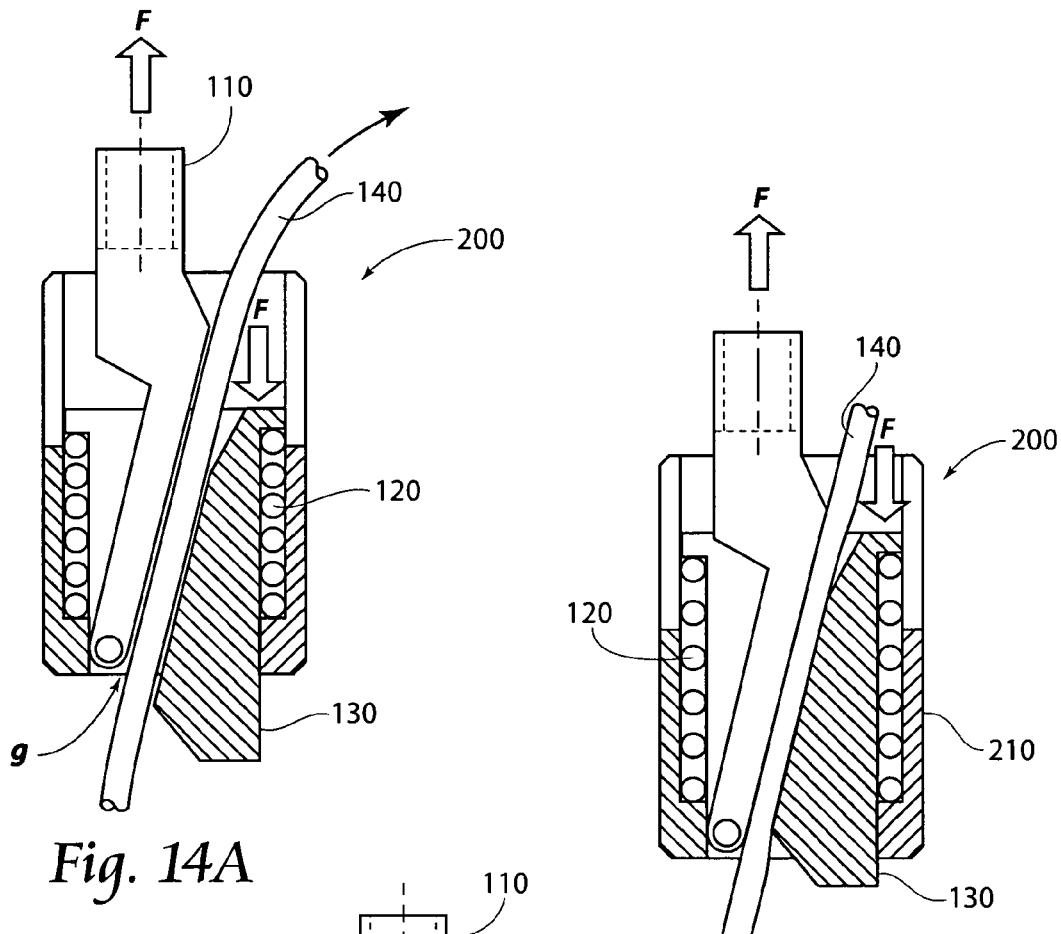
Fig. 14A
Fig. 14B
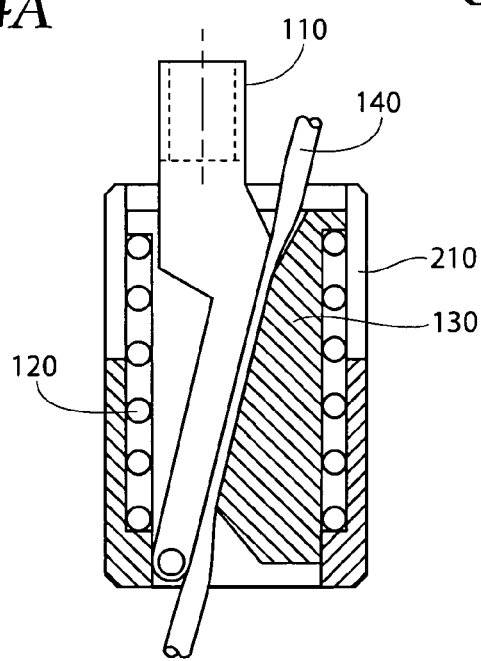
Fig. 14C

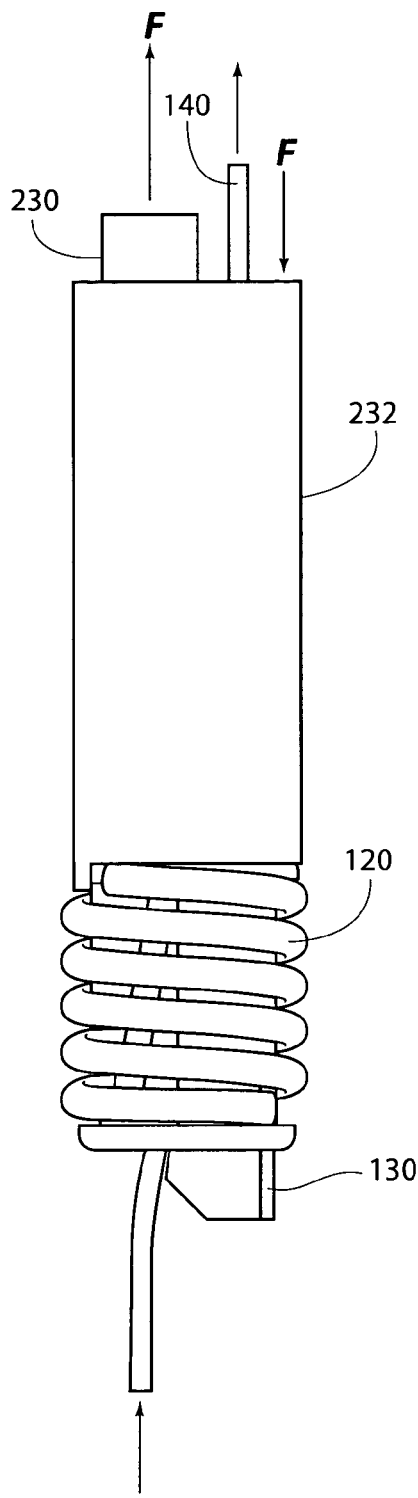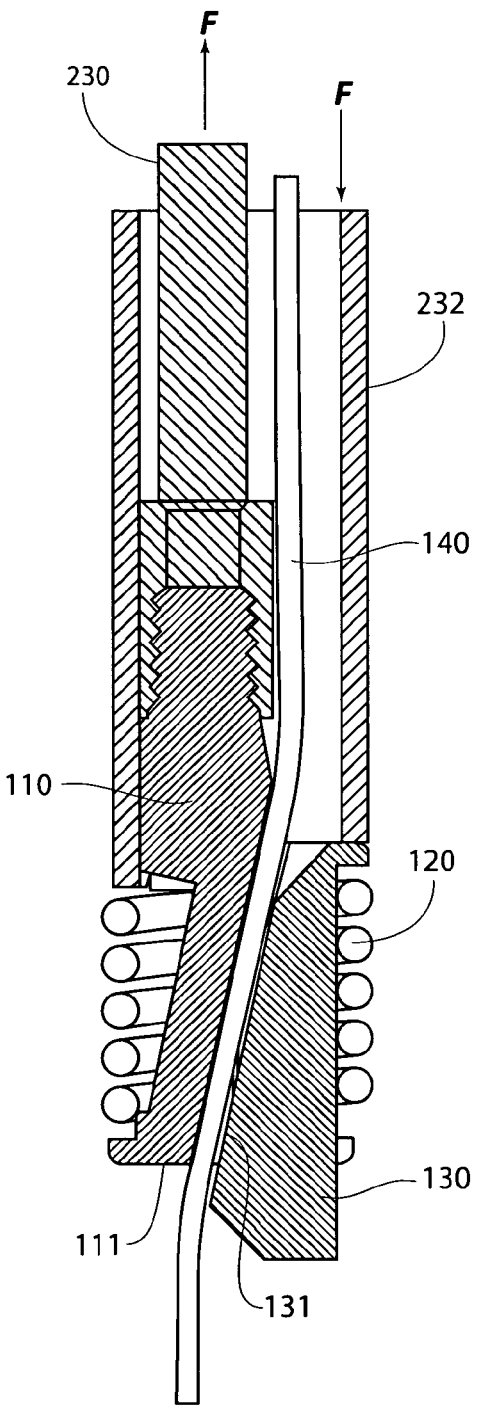
Fig. 24A
Fig. 24B

WEDGE OPERATED RETAINER DEVICE AND METHODS

This application claims the benefit of U.S. Provisional Application No. 60/701,629, filed Jul. 22, 2005, which is incorporated herein by reference in its entirety.

BACKGROUND OF THE INVENTION (a) Field of the Invention

This invention relates generally to retainers for cordage, line, twine and the like, and methods of using retainers. In particular, the invention relates to a suture retainer adapted for application on a subject by use of an introducing device, such as a catheter.

(b) Description of the Related Art

Sutures are used for a variety of surgical purposes, such as approximation of tissue and ligation of tissue. Most generally, when placing sutures, the strand of suture material to be used has a needle affixed to one end. The needle is passed through the tissue to be approximated or ligated, forming a stitch. The stitch is then tensioned appropriately, and the two ends of the suture, the needle end and the non-needle end, are knotted to retain the desired tension in the stitch. Sometimes the ends are knotted together; in other instances the ends may be stoppered or terminated separately, often with the aid of a clip or other device to form resistance to passage of the suture through tissue. While forming knots in suture during open surgery is a simple matter, forming knots in sutures during endoscopic surgery can be very difficult. For example, placing sutures during a laparoscopic procedure can require two surgeons to cooperate in a multi-step process which is performed with multiple instruments to pass the needle and suture back and forth to tie the suture knot.

Suture retainers may be used in place of suture knots to prevent passage of a suture end into and through tissue and to maintain the tension applied to the suture material during the suturing procedure. Suture clips and other suture retainers are described in the following publications: U.S. Pat. No. 5,234,449; U.S. Pat. No. 5,383,905; U.S. Pat. No. 5,391,173; U.S. Pat. No. 5,643,295; U.S. Pat. No. 5,645,553; U.S. Pat. No. 5,735,877; U.S. Pat. No. 5,845,645; U.S. Pat. No. 5,895,393; U.S. Pat. No. 5,948,001; U.S. Pat. No. 6,039,176; U.S. Pat. No. 6,896,686; U.S. Pat. No. 6,015,428; U.S. Pat. No. 6,066,160; U.S. Pat. No. 6,231,592; U.S. Pat. No. 6,432,123; and US Patent Pub No. US2004/0260344 A1.

Catheters are used for a variety of applications, such as introduction of a target device, during surgical procedures. Catheters are described in the following publications U.S. Pat. Nos. 5,643,298; 5,643,297; 5,211,651; 5,190,561; 5,156,610; 5,026,363; and 4,811,735.

Current solutions known in the art present a variety of problems for the user, including, limitations with respect to suture size, limitation in materials, inability to adjust suture tightness after placement, difficulty in removing the device, and, typically, the suture device is threaded on the suture before using. What is needed, is a suture retainer that is easier to use and that can be adjusted after placement. Further what is needed is a suture retainer that enables the user to quickly and easily work with the suture, including anchoring the suture.

SUMMARY OF THE INVENTION

The present invention provides a retainer that is quickly deployed and easy to use and that can be adjusted after placement by a user. The present invention is also directed to suture retainers. The suture retainer of this invention is suitable for percutaneous delivery, particularly where the suture retainer has a tubular profile. Other shapes can be used for other applications without departing from the scope of the invention. This invention also provides a suture retainer that can be adjusted after placement and that enables the user to handle and work with the suture quickly and easily. The suture retainer can have two opposing elements that are positioned such that the elements are juxtaposed with respect to each other. In operation the two elements are engaged by, for example, a coiled body. Additionally, a housing can be provided. The suture retainer enables termination of the suture quickly and effectively.

This invention also provides a suture retainer for terminating suture securely in a remote operating field, and is adapted for application by an introduction tool, such as a catheter, through an introduction sheath, placed for example, in the groin for percutaneous access to the femoral artery. This device and method can be used for single or multiple suture strands. The device is characterized by the juxtaposition of two wedge elements which are sprung into engagement with one another. Suture legs to be terminated are positioned between the wedges and are held securely by the spring force applied by a coiled body. Various size sutures of various materials can be accommodated between the wedges.

One aspect of the invention provides a suture retainer having first and second substantially parallel suture contact surfaces defining a suture contact axis. The suture retainer has a first position in which the suture contact surfaces are at a first distance from each other and a second position in which the suture contact surfaces are at a second distance from each other. The suture retainer is adapted to retain a suture between the first and second suture contact surfaces when in the first position. The suture retainer also has a movement guide permitting relative movement between the first and second contact surfaces along a movement axis not perpendicular to the suture contact axis.

A biasing member (such as a spring), possibly surrounding the first and second contact surfaces, may be provided to bias the first and second contact surfaces toward each other. In some embodiments, the biasing member has an axis not perpendicular to the suture contact axis. In some embodiments the first contact surface is formed on a first retainer body member and the second contact surface is formed on a second retainer body member, the biasing member being further adapted to hold the first and second body members together, such as by engaging the first body member with a first end of the spring and engaging the second body member with a second end of the spring.

In some embodiments in which the first contact surface is formed on a first retainer body member and the second contact surface is formed on a second retainer body member, the suture retainer also includes a housing in which the first and second body members are disposed.

In some embodiments in which the first contact surface is formed on a first retainer body member and the second contact surface is formed on a second retainer body member, the movement guide includes a channel in the first retainer body member. The movement guide may also include a surrounding member (such as a spring or other biasing member) retaining at least a portion of the second body member within the channel in the first body member. In some embodiments, the movement guide may also include a channel in the second retainer body member, and the surrounding member may be further adapted to retain at least a portion of the first body member in the second body member. The surrounding member may be adapted to be moved to a position permitting rotational movement between the first and second body members, e.g., to permit assembly or disassembly of the suture retainer, through, for example, a notch in the first body member.

In some embodiments, the suture retainer also has a tool engagement feature adapted to engage an actuation tool to remotely actuate the suture retainer from the first position to the second position. In embodiments in which the first contact surface is formed on a first retainer body member and the second contact surface is formed on a second retainer body member, the tool engagement feature may include a first tool engagement surface adapted to engage a first tool with the first retainer body member and a second tool engagement surface adapted to engage a second tool with the second retainer body member.

In some embodiments, the suture retainer may have a suture engaging extension from the first contact surface, such as a tooth.

In some embodiments, the suture retainer also has third and fourth substantially parallel suture contact surfaces defining a second suture contact axis, the third and fourth suture contact surfaces being at a first distance from each other to retain a suture when the suture retainer is in the first position and at a second distance from each other when the suture retainer is in the second position. The suture retainer of this embodiment may also include a ridge separating the first and third suture contact surfaces.

Another aspect of the invention provides a method of retaining a surgical suture including the following steps: placing a suture between first and second substantially parallel suture contact surfaces of a suture retainer, the first and second contact surfaces defining a distance between them, one of the first and second contact surfaces defining a suture contact axis; and moving at least one of the first and second contact surfaces along a movement axis not perpendicular to the suture contact axis to reduce the distance between the first and second suture contact surfaces to engage the suture in the retainer. In some embodiments, the method includes the step of increasing the distance between the first and second contact surfaces prior to the placing step. In embodiments in which the suture retainer has a biasing member adapted to bias the first and second contact surfaces toward each other, the increasing step includes the step of applying an opening force to move at least one of the first and second contact surfaces against the biasing member bias. The second moving step of the method may also include the step of removing the opening force.

In some embodiments, after engaging the suture in the suture retainer, the method includes the step of increasing the distance between the first and second contact surfaces to release the suture from the suture retainer. The method may also include the step of, after releasing the suture from the suture retainer, moving at least one of the first and second contact surfaces along a movement axis not perpendicular to the suture contact axis to reduce the distance between the first and second suture contact surfaces to re-engage the suture in the retainer. The method may also include the step of, after releasing the suture from the suture retainer, moving the suture relative to the suture retainer prior to re-engaging the suture in the suture retainer. In still other embodiments, the step of increasing the distance includes the step of engaging a tool with the suture retainer and using the tool to remotely increase the distance between the first and second contact surfaces.

Yet another aspect of the invention provides a method of retaining a surgical suture including the steps of placing a suture between first and second substantially parallel suture contact surfaces of a suture retainer; and applying a compressive force on the suture with the contact surfaces to engage the suture in the retainer, the compressive force having a force vector that is greatest in a direction not substantially perpendicular to the contact surfaces.

Still another aspect of the invention provides a suture retainer having first and second substantially parallel suture contact surfaces, a movement guide permitting relative movement between the first and second contact surfaces and a biasing member, the contact surfaces, movement guide and biasing member being adapted to bias the first and second surfaces toward each other to apply a force vector to a suture disposed between the contact surfaces that is greatest in a direction not substantially perpendicular to the contact surfaces.

Other embodiments of the invention will be apparent from the detailed description and drawings.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A illustrates the suture retainer having a notched body removably located within a coiled body with an opposing body positioned above the notched body; FIG. 1B is a cross-sectional view of the assembled suture retainer; FIG. 1C is a cross-sectional view of the suture retainer assembly of FIG. 1B at section 1C; FIG. 1D is a cross-sectional view of the assembled suture retainer with the coiled body where the coiled body has been compressed to enable movement of one or both of the notched body and opposing body to create a gap between the bodies for passage of a suture; FIG. 1E is a cross-sectional view of the assembled suture retainer with the coiled body partially released illustrating the notched body and opposing body engaging the suture; FIG. 1F illustrates a cross-sectional view of the assembled suture retainer with the coiled body fully released wherein the notched body and opposing body completely engage the suture; FIG. 1G illustrates a cross-sectional view of the assembled suture retainer having a force diagram superimposed thereon to illustrate the force placed on the suture by the notched body and the opposing body of the suture retainer when the suture retainer is deployed.

FIGS. 9A-B illustrate a side view and cross-sectional view of the combination of elements comprising the suture retainer with the coiled body released, the opposing body positioned within the cavity formed between the notched body and the coiled body, and the notched body rotated toward the central axis of the coiled body.

FIGS. 10A-B are partial cross-sectional views of a suture retainer according to an alternate embodiment the invention, with the suture retainer having a housing; FIG. 10A illustrates the suture retainer having a notched body removably located within a coiled body and a housing with an opposing body positioned above the notched body; FIG. 10B is a partial cross-sectional view of the assembled suture retainer; FIG. 10C is a cross-sectional view of the suture retainer assembly of FIG. 10B at section 10C.

FIG. 13 additionally shows alternate attachment means and suture passage in the notched body.

FIG. 14A is a partial cross-sectional view of the assembled suture retainer with the housing where the coiled body has been compressed to enable movement of one or both of the notched body and opposing body to create a gap between the bodies for a suture; FIG. 14B is a partial cross-sectional view of the assembled suture retainer with the coiled body partially released illustrating the notched body and opposing body engaging the suture; FIG. 14c illustrates a partial cross-sectional view of the assembled suture retainer with the coiled body released wherein the notched body and opposing body completely engage the suture.

FIG. 24A illustrates a suture retainer according to the invention which is engaged with a suture, where the retainer is in an open position; FIG. 24B is a cross-section of the retainer shown in FIG. 24A showing the coiled body compressed to relieve the force on the suture from the notched body and the opposing body.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. As will be appreciated by those of skill in the art, various alternatives to the embodiments of the invention described herein may be employed in practicing the invention. It is intended that the following claims define the scope of the invention and that methods and structures within the scope of these claims and their equivalents be covered thereby.

Figure 1A:
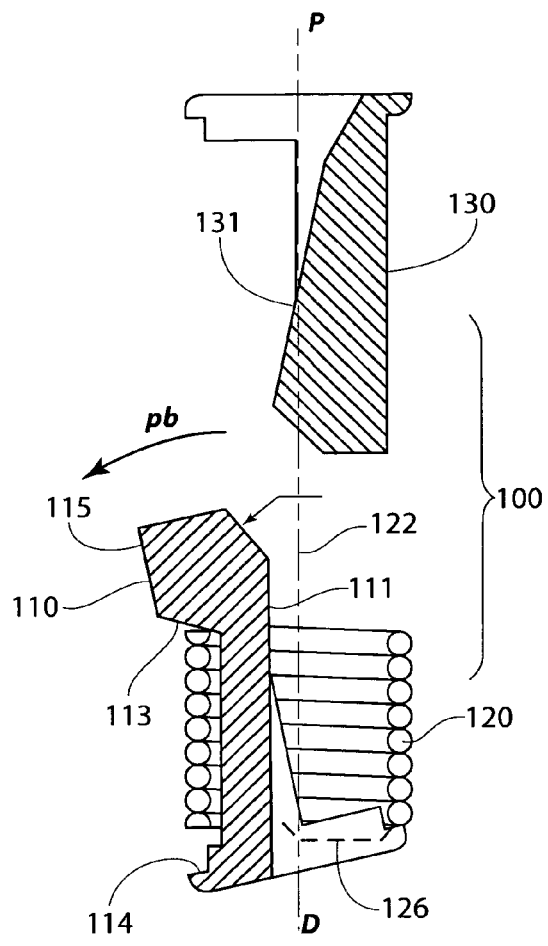
FIGS. 1A-G are cross-sectional views of a suture retainer according to the invention.

The present invention is directed to a suture retainer 100 having a proximal end P and a distal end D. The basic components comprising the suture retainer are shown in FIGS. 1A-G. FIG. 1A illustrates the suture retainer 100 having a notched body 110 removably located within a coiled body 120 (e.g., a spring or other biasing member) in a compressed state. Because the coiled body 120 is compressed, the notched body 110 can be positioned, as illustrated, so that the notched body 110 is pivoted pb away from the central axis 122 of the coiled body 120 and such that the flange 114 of the notched body does not engage the coiled body 120 on all sides. In this illustration, an opposing body 130 is positioned above the notched body 110 and coiled body 120, at the proximal end P, in preparation for insertion into space 126 between notched body 110 and coiled body 120. For purposes of describing the invention proximal P and distal D are used to describe one end of the suture retainer, or its component parts, with respect to the other end. Nothing with respect to the use of proximal and distal herein to describe the invention should in any way limit the device, e.g., to a particular orientation. It will also be appreciated by those of skill in the art that each of the notched body 110 and the opposing body 130 can be described in other terms which are equally descriptive. For example, the bodies can be described as opposing wedges, or a wedge and anvil. Use of the terms notched body and opposing body to describe the bodies and their relationship and interaction in no way limits the scope of the disclosure provided.

Figure 1B:
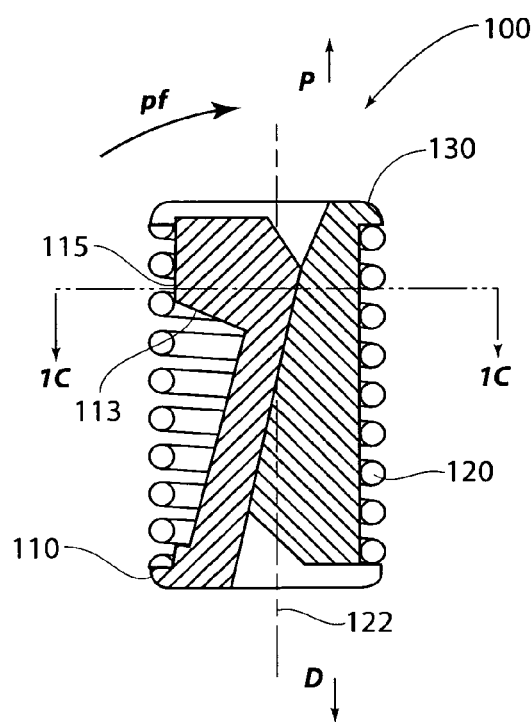
Figure 1C:
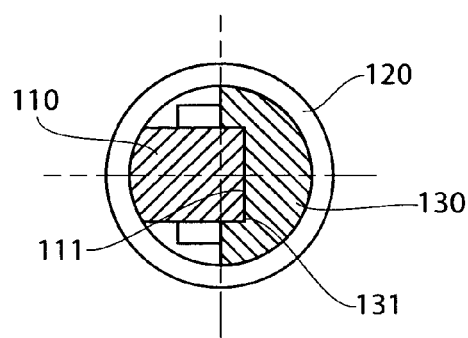

FIG. 1B is a cross-sectional view of the suture retainer 100 shown in FIG. 1A where the opposing body 130 engages the coiled body 120 and the notched body 110. As shown in FIG. 1B once the opposing body 130 is inserted and engaged, the notched body 110 is pivoted forward pf toward the central axis 122 of the coiled body 120 causing the inclined opposing faces 111, 131 (shown in FIG. 1A) of the notched body 110 and the opposing body 130 to come into contact. Releasing the coiled body 120 completes the assembly of the suture retainer 100. Once the coiled body 120 is released, the proximal end 115 of notched body 110 is in contact with the inside of the coiled body 120 and is held in alignment, and the components of the suture retainer 100 cannot be disassembled without compressing the coiled body 120 past the notch 113, of the notched body 110, pivoting the notched body 110 away from the central axis 122 and then removing the opposing body 130, proximally and the notched body 110, distally. The proximal end 115 of notched body 110 prevents inadvertent disassembly of the device when the suture retainer 100 has been deployed, or is in use. In addition, the presence of coiled body 120 around notched body 110 and opposing body 130 holds the suture retainer together even if no suture is present. Moreover, the interacting components of the device act as a movement guide between the two bodies. FIG. 1C is a cross-sectional view of the suture retainer of FIG. 1B at section 1C showing opposing faces 111, 131 in contact.

Candidate materials for the suture retainer elements would be known by persons skilled in the art and include, for example, suitable biocompatible materials such as metals (e.g. stainless steel, nitinol) and engineering plastics (e.g. polycarbonate). Although the coiled body 120 can be formed from, for example, a compression sleeve, it is anticipated that typically the coiled body 120 is formed from a metallic substance formed into a spring to obtain optimal spring force for the assembly. However any structure capable of providing a biasing force to the device will be suitable, as will be appreciated by those of skill in the art.

Figure 1D:
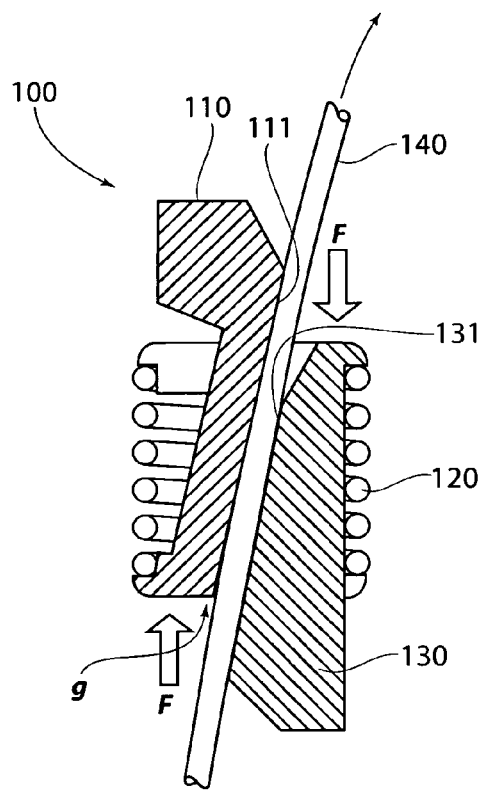
Figure 1E:
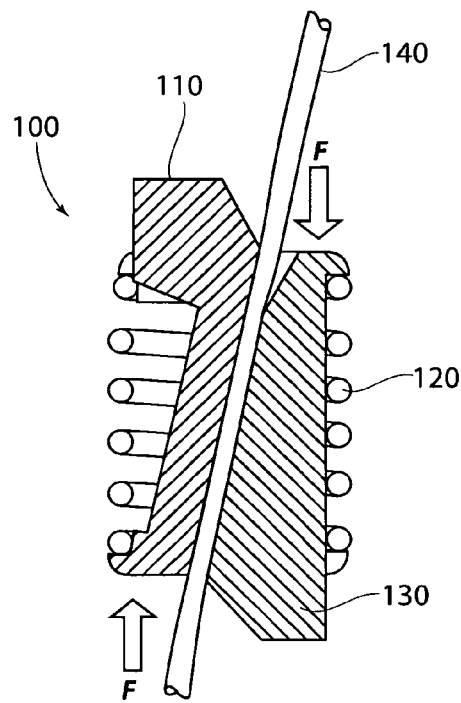
Figure 1F:
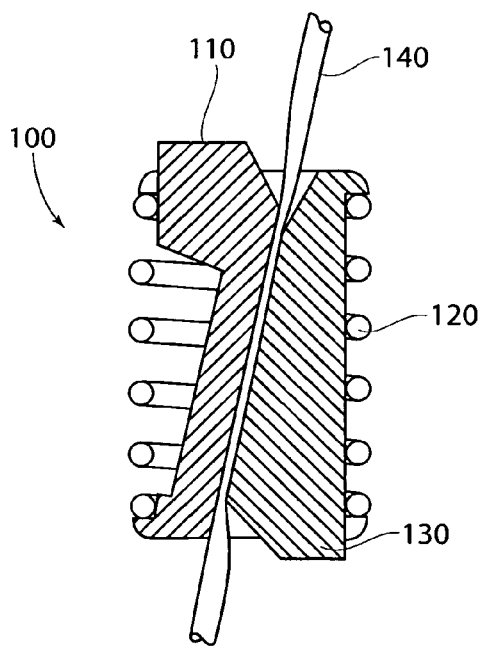

Turning to the operation of the suture retainer 100, FIG. 1D is a cross-sectional view of the assembled suture retainer 100 where the coiled body 120 has been compressed by opposing forces F on notched body 110 and opposing body 130 to move one or both bodies along a movement axis to create a gap g between the bodies for a suture 140. As the coiled body 120 is released, the suture contact surfaces 111, 131 of the assembled suture retainer 100 (which lie along a suture contact axis) engage the suture 140, as illustrated in FIG. 1E. As the suture contact surfaces 111, 131 move toward each other, the suture 140 begins to be engaged by the suture retainer 100 and movement of the suture 140 becomes more difficult as additional force is applied by the coiled body 120. Once the coiled body 120 is fully released, the notched body 110 and opposing body 130 completely engage the suture 140 between the inclined opposing faces 111, 131, as shown in FIG. 1F and exert a force on the suture 140 that prevents, or tends to prevent, movement of the suture 140 within the suture retainer 100. The force is preferably applied without damaging the suture 140.

Figure 1G:
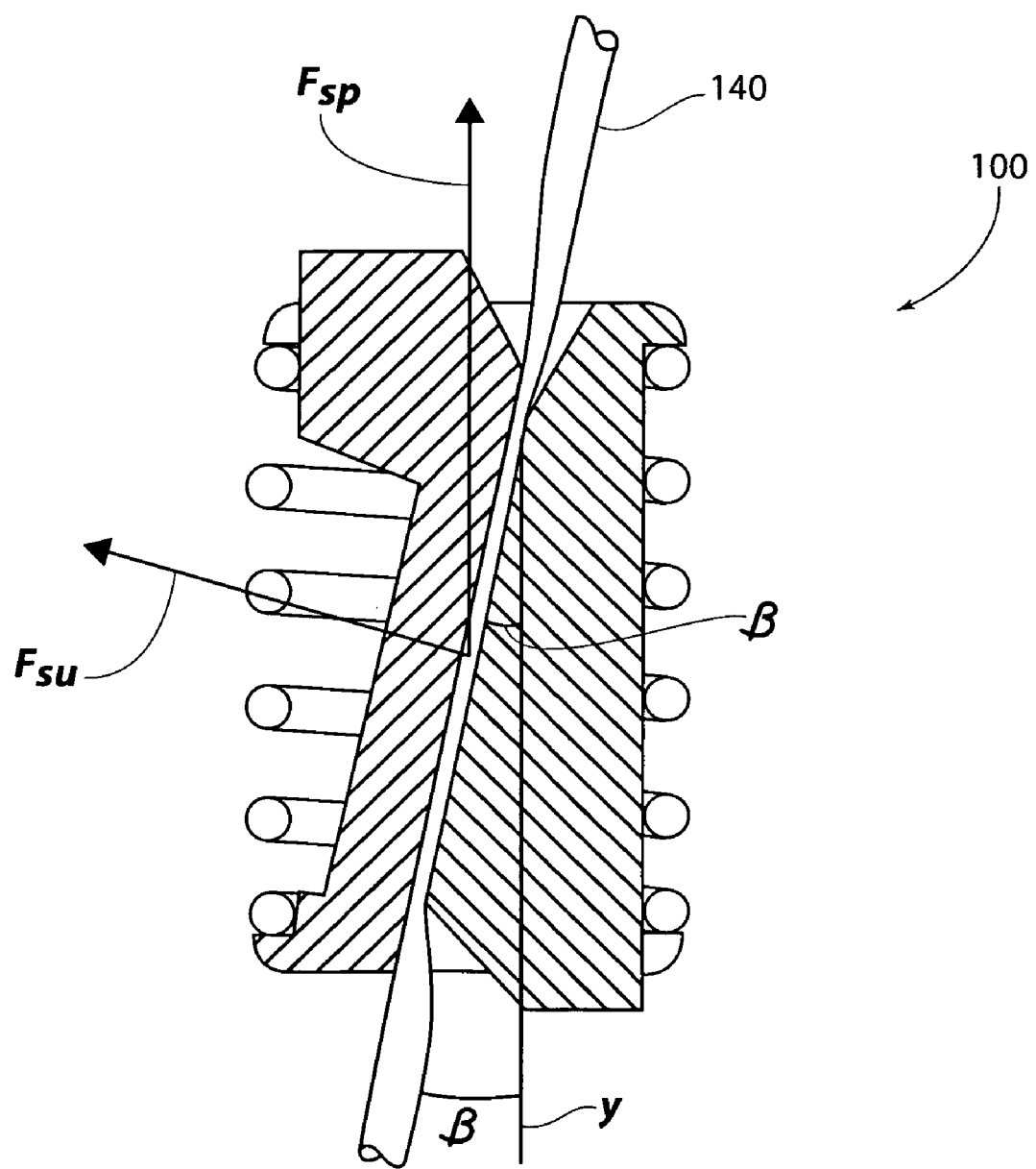

FIG. 1G illustrates a cross-sectional view of the assembled suture retainer 100 having a force diagram superimposed thereon to illustrate the force placed on the suture 140. The design of the suture retainer 100 takes mechanical advantage of a wedge effect by creating pressure between the two suture contact surfaces (opposing faces 111, 131 shown in FIG. 1D). The effect results in the force on the suture ($F_{su}$) being equal to the axial spring force ($F_{sp}$) divided by the sine of the inclination of the suture contact axis defined by the contact surfaces (β) off the movement axis (y) of the spring (ignoring frictional forces between the component parts):

$$F_{su} = \frac{F_{sp}}{\sin\beta}$$

As will be appreciated by those of skill in the art, the force on the suture ($F_{su}$) can be increased by either increasing the spring force ($F_{sp}$) and/or by decreasing sin β by decreasing the angle β between the movement axis y and the suture contact axis defined by inclined surfaces 111, 131. The force on the suture ($F_{su}$) can also be decreased by either decreasing the axial spring force ($F_{sp}$) and/or by increasing sin β by increasing the angle β between the movement axis y and the suture contact axis of inclined surfaces 111, 131. As will also be appreciated by those of skill in the art, the force on the suture ($F_{su}$) with any angle β less than 90° is greater than just the spring force ($F_{sp}$).

Figure 2:
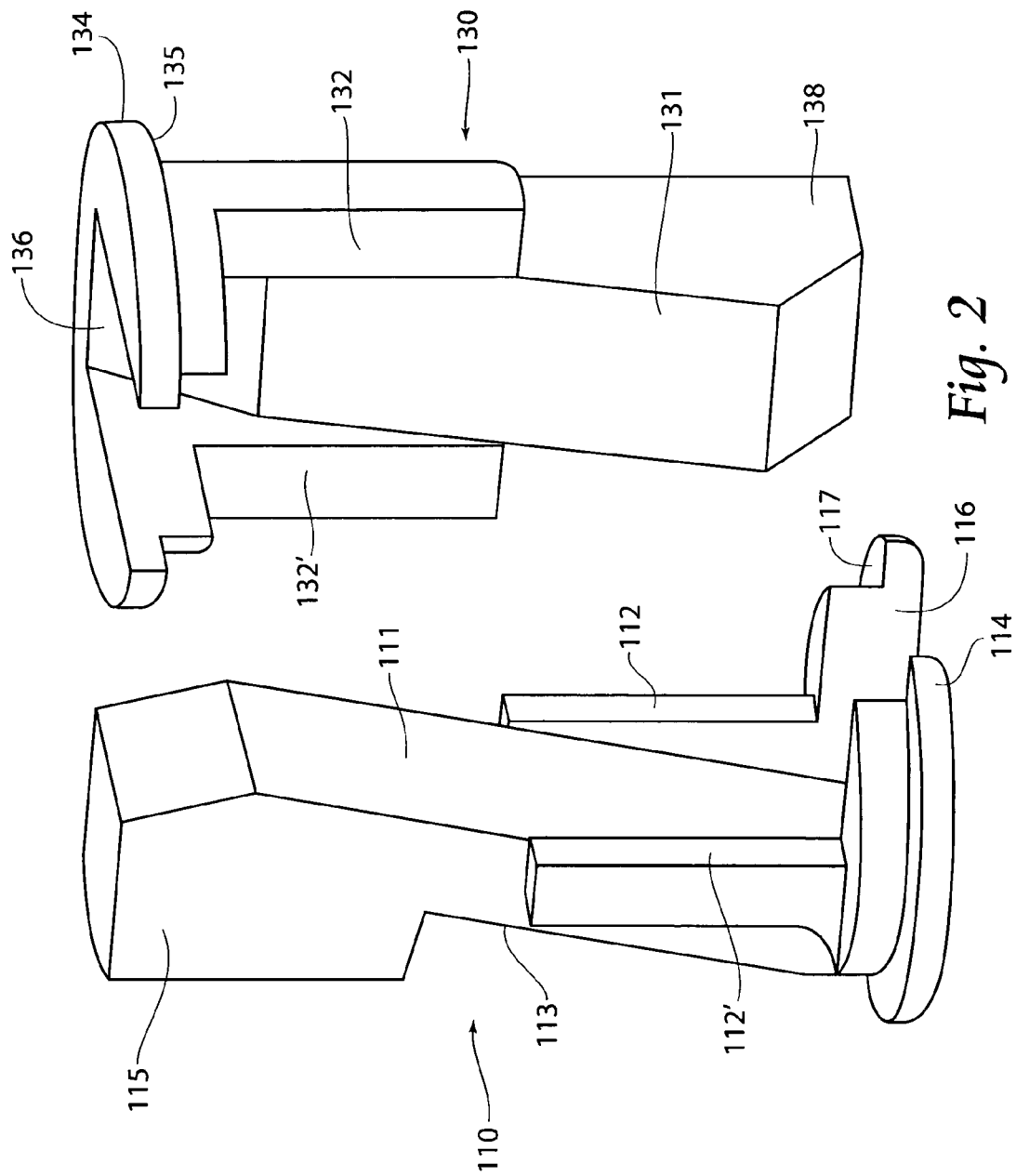
FIG. 2 is a perspective view of the notched and opposing bodies of the suture retainer in FIG. 1 shown juxtaposed.

FIG. 2 is a perspective view, for illustration purposes, of the notched body 110 and the opposing body 130 of the suture retainer 100 shown in FIG. 1. The notched body 110 and the opposing body 130 each have an inclined opposing faces 111, 131 and two parallel surfaces 112, 112' 132, 132'. The parallel surfaces 112, 112', 132, 132' are provided to keep the suture 140 positioned between the inclined opposing faces 111, 131. Surfaces 112, 112' 131, 131' lie closely about central plane containing central axis 122 when the components are assembled. Flanges 114, 134 are provided at one end of each body 110, 130 to engage the coiled body 120. Each flange 114, 134, has an upper surface and a lower surface, one of which faces interiorly toward the center of the device. The interiorly facing surfaces 117, 135 of the flanges 114, 134 engage the coiled body 120. The flanges 114, 134 also have respective channels 116, 136 which engage the distal end 138 of the opposing body 130 and the proximal end 115 of the notched body 110 respectively. These elements cooperate to form a movement guide for the two bodies of the device.

Figure 3:
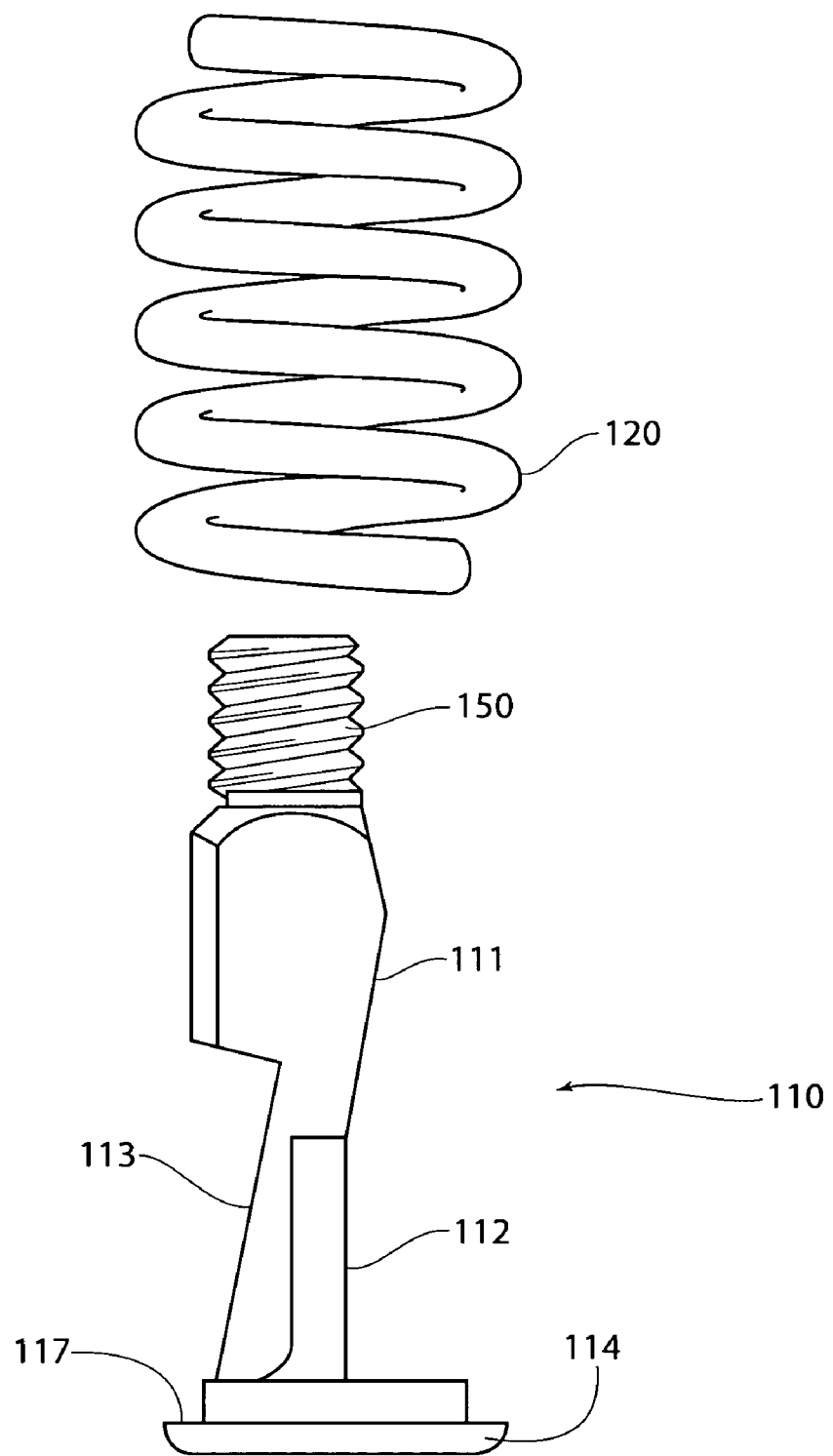
FIG. 3 is an exploded view of the notched and coiled bodies of the suture retainer in FIG. 1

FIG. 3 is an exploded view of component elements comprising a suture retainer 100 according to an embodiment of this invention. The notched body 110 is illustrated showing a notch 113 above a flange 114 which is located at the distal end of the retainer 100. The inclined face 111 is positioned on a side opposite the notch 113 and adjacent parallel surfaces 112 (and 112' not shown) forming a channel, or pair of cheeks, between which the suture 140 is retained. An optional male threaded connector 150 can be provided to cooperate with a control mechanism, as will be discussed below with respect to the embodiments illustrated in FIGS. 15-16. The coiled body 120 is positioned in FIG. 3 such that it can be deployed over the notched body 110. Each of the spring ends can be configured such that it is squared and ground to maximize contact of the spring end with the flange 114 and interiorly facing surface 117.

Figure 4A:
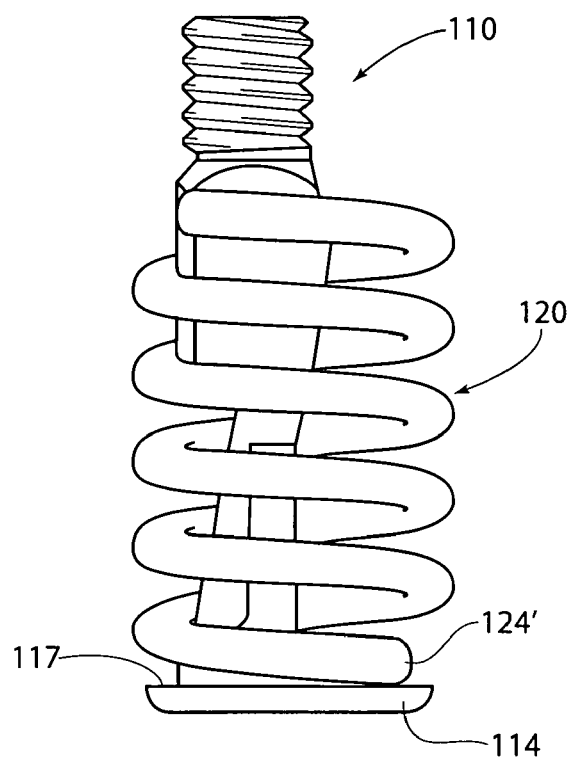
FIGS. 4A-B illustrate a side view and cross-sectional view of the assembled elements of the suture retainer shown in FIG. 3.
Figure 4B:
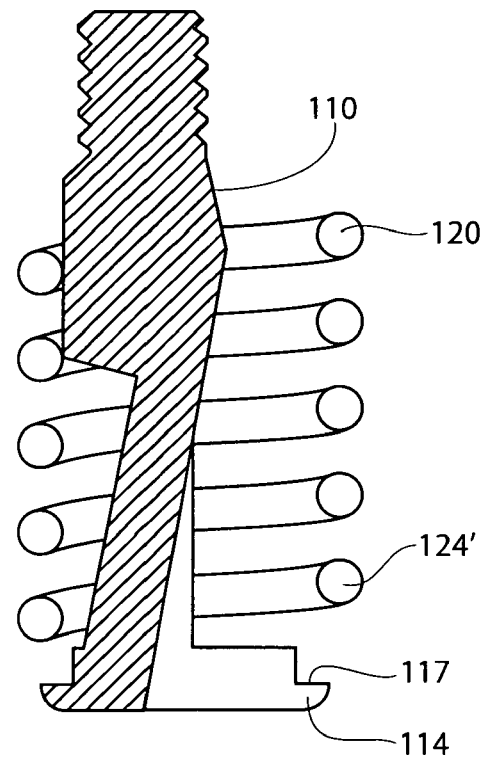

Turning now to FIG. 4A-B, which further illustrates a side view and cross-sectional view of the combination of the notched body 110 and the coiled body 120 of the suture retainer 100 show in FIG. 3. As illustrated, the flange 114 of the notched body 110 is configured to provide an interiorly facing surface 117 for a coil 124' of the coiled body 120 to be seated thereon.

Figures 5A, 5B:
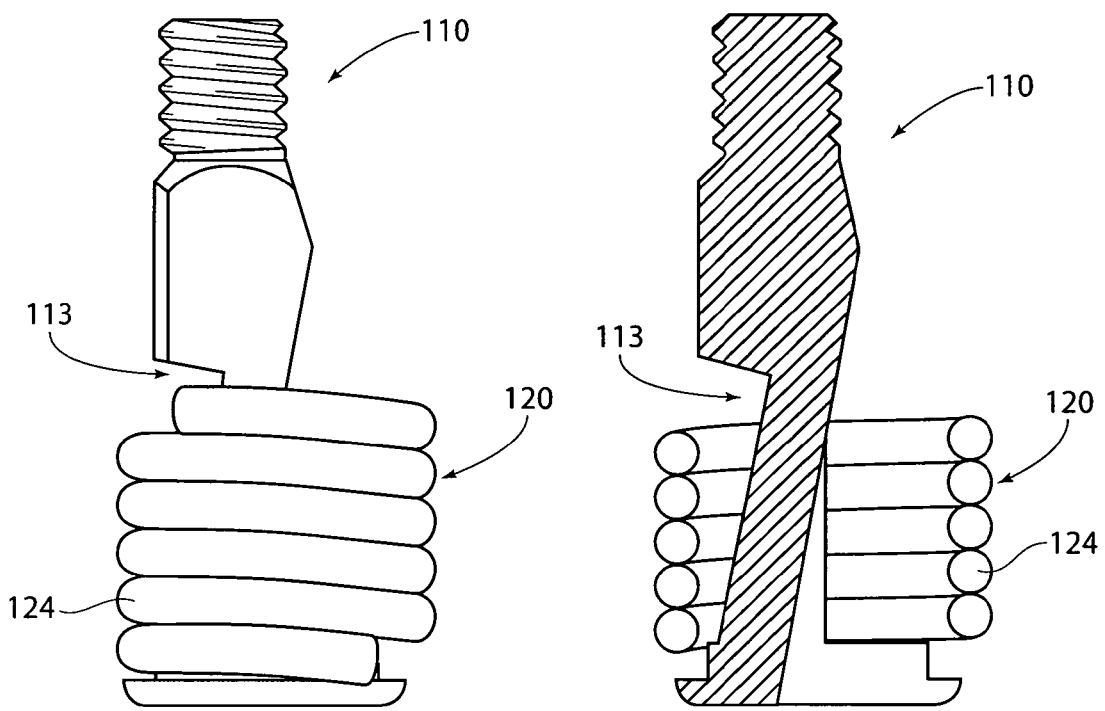
FIGS. 5A-B illustrate a side view and cross-sectional view of the combination of elements of the suture retainer shown in FIG. 3, with the coiled body compressed.

In order to begin assembling the suture retainer, as shown in FIGS. 5A-B the coiled body 120 is compressed such that the coils 124 of the coiled body come into proximity with each other and the proximal most coil is positioned such that when the notched body 110 is tilted off the central axis 122 of the coiled body 120 the coils 124 fit within the notch 11 the notched body 110. FIG. 5B better illustrates, in cross-section, how the notch 113 of the notched body 110 can accommodate the compressed coiled body 120 upon rotation of the notched body 110 off the central axis of the coiled body 120.

Figure 6A:
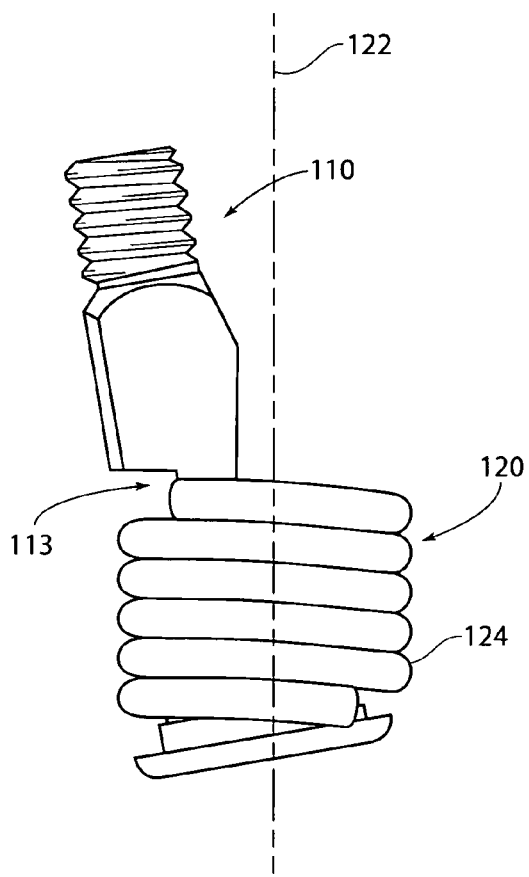
FIGS. 6A-B illustrate a side view and cross-sectional view of the combination of elements of the suture retainer of FIG. 3 with the coiled body compressed and the notched body rotated away from the central axis of the coiled body.
Figure 6B:
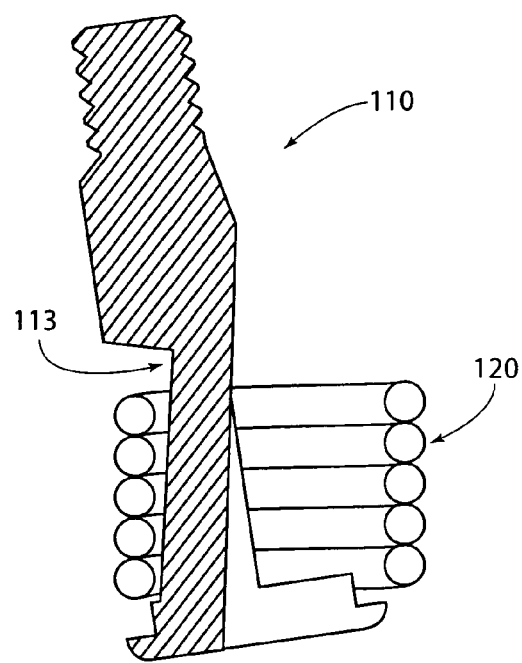

FIGS. 6A-B illustrate a side view and cross-sectional view of the coiled body 120 (from the step shown in FIG. 5) with the notched body 110 rotated away from the central axis 122 of the coiled body 120 such that the coils 124 sit within the notch 113.

Figure 7A:
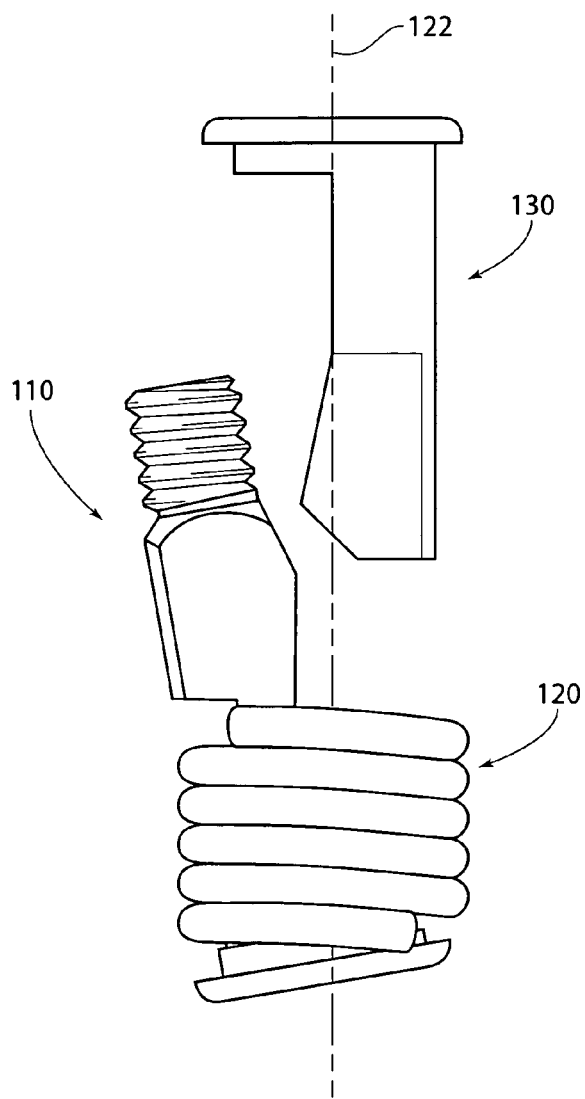
FIGS. 7A-B illustrate a side view and cross-sectional view of the combination of elements comprising the suture retainer with the coiled body compressed, the notched body rotated away from the central axis of the coiled body, and the opposing body positioned to be inserted into the cavity between the notched body and the coiled body.
Figure 7B:
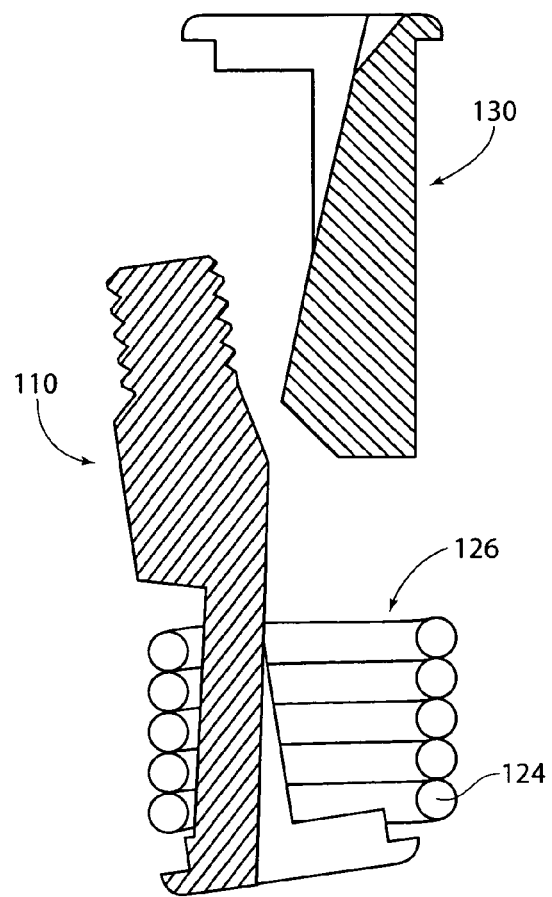

FIGS. 7A-B illustrate in side view and cross-sectional view the coiled body 120, the notched body 110 rotated away from the central axis 122 of the coiled body 120, and the opposing body 130 positioned to be inserted into the space 126 between the notched body 110 and the coiled body 120.

Figure 8A:
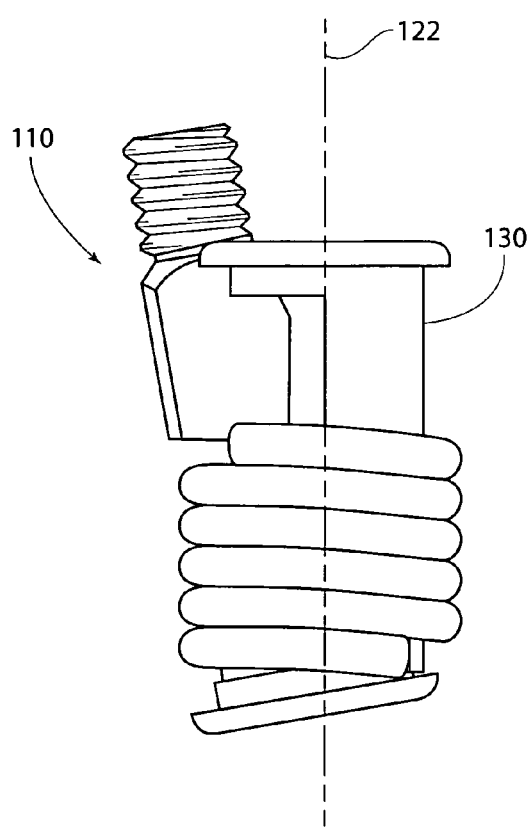
FIGS. 8A-B illustrate a side view and cross-sectional view of the combination of elements comprising the suture retainer with the coiled body compressed, the notched body rotated away from the central axis of the coiled body, and the opposing body positioned in the space between the notched body and the coiled body.
Figure 8B:
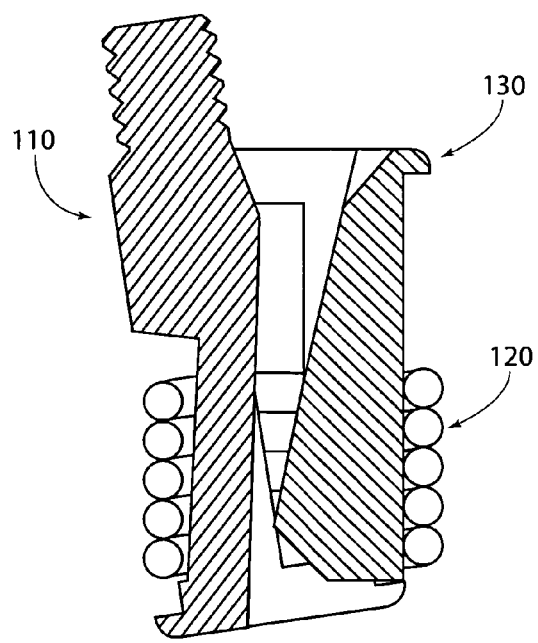

FIGS. 8A-B illustrates in side view and cross-sectional view, the compressed coiled body 120, surrounding the notched body 110 which continues to be rotated away from the central axis 122 of the coiled body 120. At this point, the opposing body 130 has been positioned within the space 126 shown in FIG. 7 ready for rotation of notched body 110 toward central axis 122 and release of coiled body 120.

FIGS. 9A-B illustrates in side view and cross-sectional view, the assembled suture retainer 100 with the notched body 110 and the opposing body 130 positioned adjacent each other such that the inclined opposing surfaces 111, 131 are forcibly engaged. The coiled body 120 has been released so that the coils 124 have expanded and an upper coil 125 engages a interiorly facing surface 135 of the flange 134 of the opposing body 130 and the lower coil 127 engages a interiorly facing surface 117 of the flange 114 of a notched body 110. Additionally, the notched body 110 has rotated into the channel 136 of the opposing body 130 and proximal end 115 of notched body 110 is in contact with the inside of coiled body 120.

FIGS. 10A-B are partial cross-sectional views of a suture retainer 200 according to an alternate embodiment the invention, wherein the suture retainer 200 has a housing 210 in which the coiled body 120, notched body 110 and opposing body 130 are contained. As with the previous embodiment, the opposing body 130 and notched body 120 are removably located within a coiled body 120 which is removably contained within the optional housing 210. The optional housing 210 of this embodiment provides a smooth exterior profile that might be advantageous in some applications. FIG. 10B is a partial cross-sectional view of the assembled suture retainer 200 having the optional housing 210. FIG. 10C is a partial cross-sectional view of the suture retainer 200 assembly of FIG. 10B the sectional line 10C.

Figure 11A:
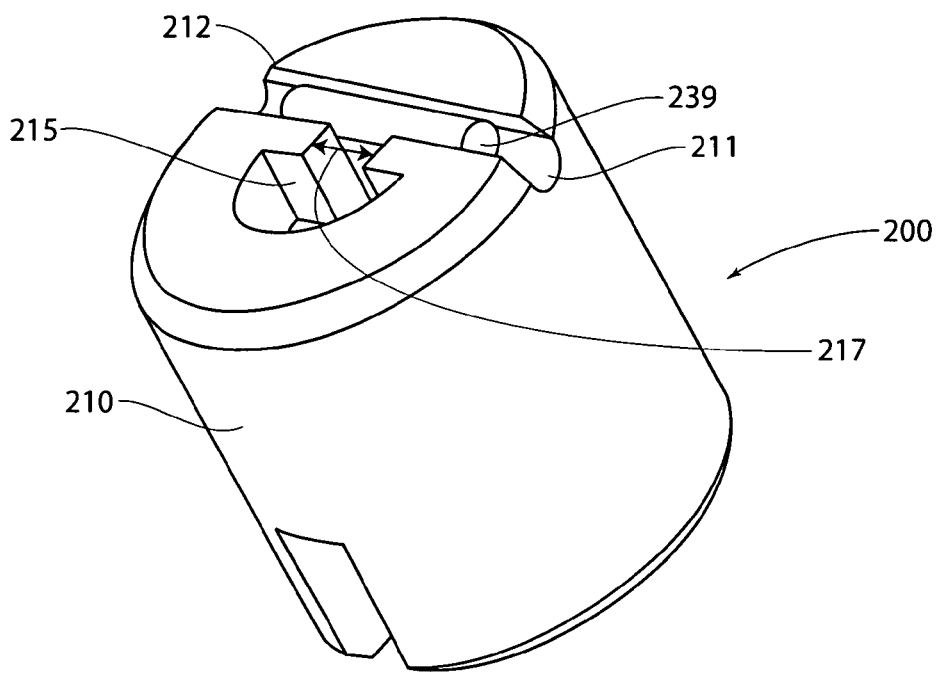
FIGS. 11A-B are perspective views of an assembled suture retainer of FIG. 10.
Figure 11B:
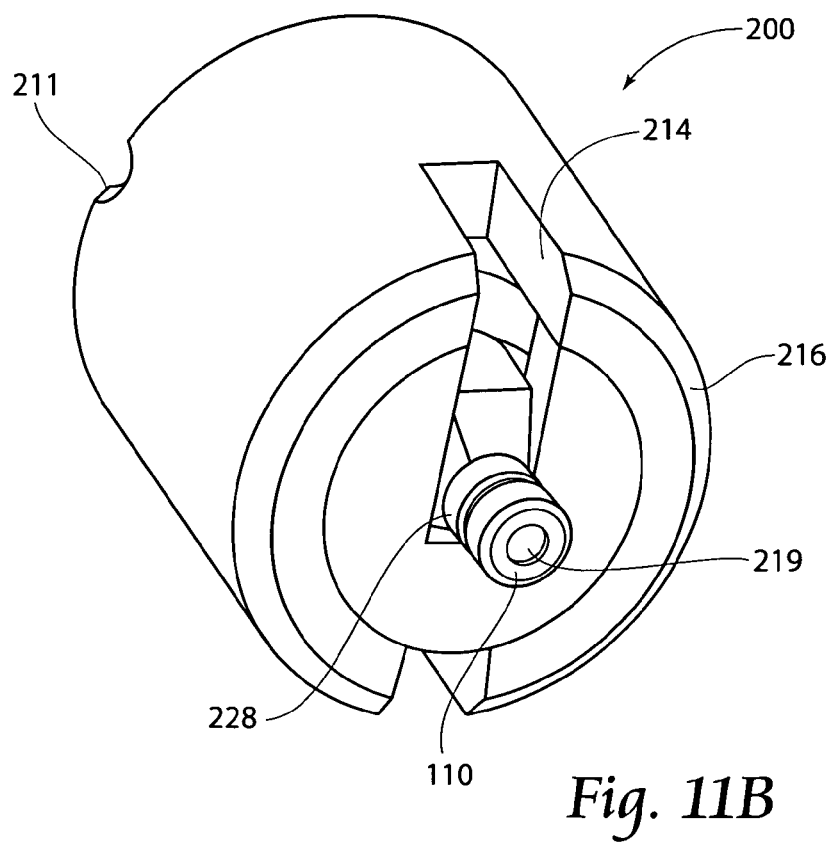

FIG. 11A is a perspective view of the distal end of the suture retainer 200. In this depiction, at-shaped pivot pin 239 located on the distal end of the notched body 110 is shown. The t-shaped pivot pin 239 is located within a pin channel 211 on the distal surface 212 of the housing 210. The notched body 110 is inserted into the housing 210 by passing through opening 215 and slot 217 which are located on distal surface 212. As shown in FIG. 11B slots 214 are provided on the proximal surface 216 through which the proximal end of the notched body 110 is positioned. As illustrated, the slots 214 are configured such that they have a perpendicular orientation to pin channel 211. FIG. 11B illustrates the proximal view including an optional notched extension 228 and aperture 219 (further disclosed in FIG. 22B) through the proximal end of the notched body 110.

Figure 12:
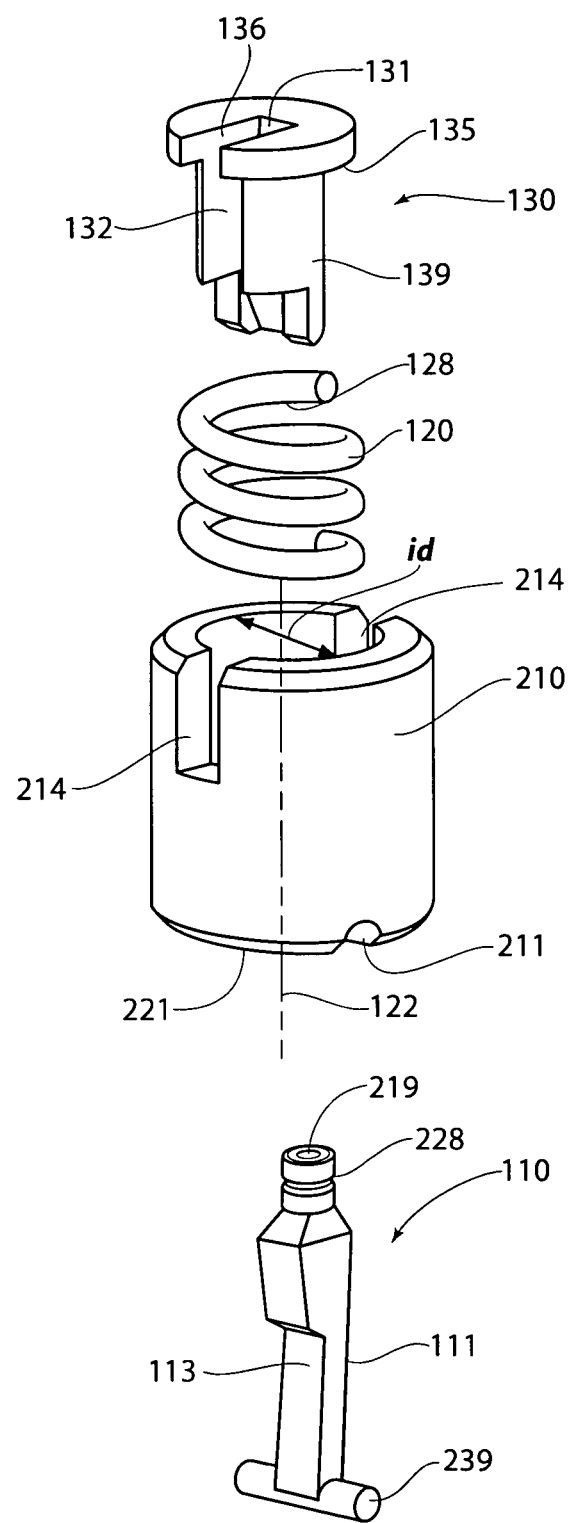
FIG. 12 is an exploded view of the elements of the suture retainer shown in FIG. 11 according to an embodiment of the invention.

FIG. 12 illustrates the components of the suture retainer 200 shown in FIG. 11 in an exploded view. An opposing body 130 is configured to fit within the housing 210 which is a hollow, cylindrical body. The opposing body 130 has a channel 136 that can be oriented to align with one of the slots 214 on the housing 210. When the channel 136 is aligned with a slot 214, then the proximal end of the notched body 110 can pivot within the slot 214 and channel 136.

The housing 210 also houses a coiled body 120. In operation, the coiled body 120 is, for example, a compression spring which forces the notched body 110 into engagement with the opposing body 130 of the suture retainer 200. As illustrated, the inner diameter id of the housing 210 accommodates the coaxial action of the coiled body 120. The cylindrical body of the housing 210 can have an inner circumferential ledge 221 at its distal end to engage and support the distal end of the coiled body 120. At the distal end of the housing 210 is a cut-out in the form of a pin channel 211. Opposite sides of the pin channel 211 accommodate the t-shaped pivot pin 239 of the notched body 110. Slot 217 functions to locate notched body 110 centrally. The pin channel 211 transfers force to the notched body 110 when the housing 210 is acted upon by the coiled body 120 or it transfers force to the housing 210 when the notched body 110 is acted upon by an outside force F.

The opposing body 130 has an inclined face 131 which comprises a suture contact surface and, in the absence of a suture being inserted into the retainer, contacts a similar inclined face 111 of the notched body 110.

When assembled, the outer wall 139 of the opposing body 130, contacts the inner contact surface 128 of the coiled body 120. Close-fitting extensions, or lips, 112 such as those shown in FIG. 3 can be provided adjacent and perpendicular to the truncated notched body 110 to keep the suture legs contained between the mating suture contact surfaces.

The suture retainer 200 of this embodiment is assembled as follows. The coiled body 120 is inserted proximally into the housing 210 and compressed fully. The coiled body 120 is held compressed through the slots 214 in the housing 210. The notched body 110 is then inserted from the distal end into the housing 210 through opening 215 and slot 217 and the pivot pin 239 is engaged within pin channel 211. The notched body 110 is then rotated away from the central axis 122 of the coiled body 120 with the proximal end of the notch above the compressed spring, into slot 214 and held in place. The opposing body 130 is then inserted from the proximal end into the housing 210, into the space between the notched body 110 and the coiled body 120. Thereafter, the coiled body 120 is released and the notched body rotated back toward the axis 122 of the coiled body 120. The assembly is then complete.

Figure 13A:
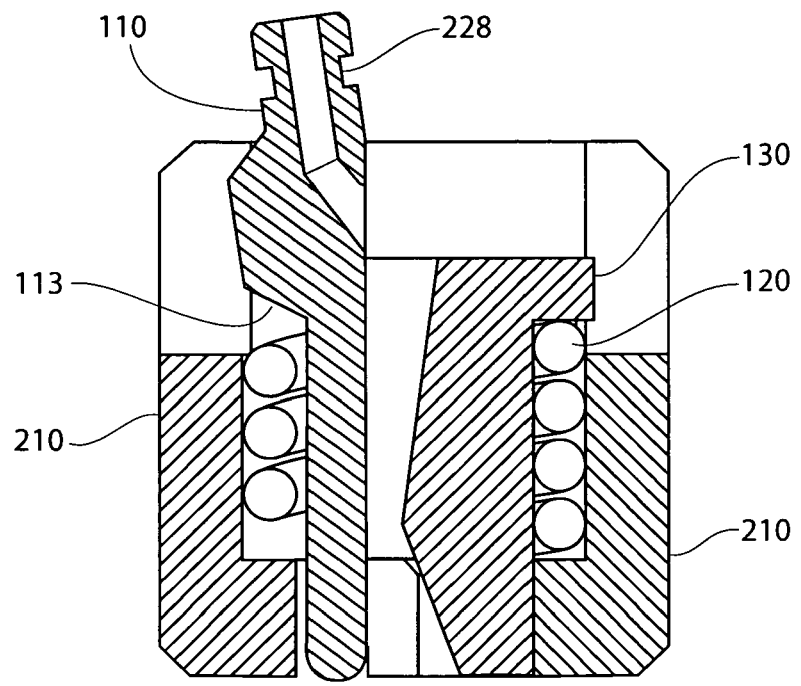
FIG. 13A is a cross-sectional view of the assembled suture retainer shown in FIG. 10 according to an embodiment of the invention where the notched body is rotated away from the central axis of the coiled body.

FIG. 13A is a sectional view of a suture retainer 200 according to an embodiment of the invention where the suture retainer 200 is in the open assembly position with the notched body 110 rotated away from the central axis 122 of the coiled body 120. As the suture retainer 200 is loaded, the coiled body 120 can be compressed, e.g., using a tool through slots 214. When the notched body 110 rotates off the central axis 122 of the coiled body 120 a space is created between the notched body 110 and the coiled body 120, and the opposing body 130 can be inserted. The notched body 110 then can rotate toward the central axis 122 of the coiled body 120 which enables the coiled body 120 to move beyond the shoulder notch 113. Side slots 214 can be provided to enable a tool to hold the coiled body 120 in a compressed position during assembly and to allow rotation of notched body 110.

Figure 13B:
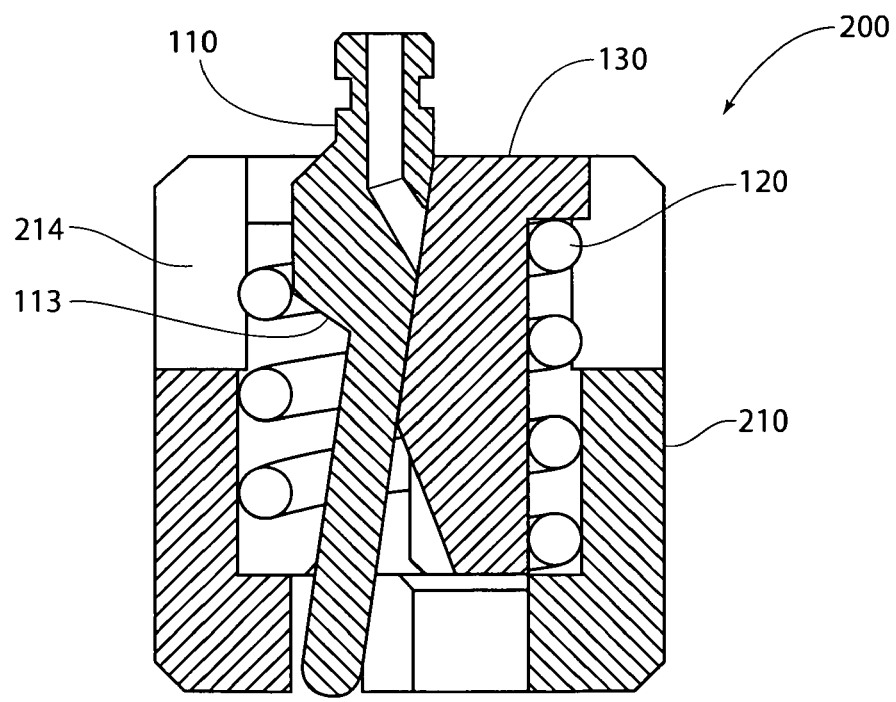
FIG. 13B is a cross-sectional view of the assembled suture retainer, where the notched body has been rotated toward the central axis of the coiled body.

FIG. 13B is a sectional view of a suture retainer shown in FIG. 13A wherein the suture retainer is in the locked, or closed, position with the notched body 110 rotated toward the central axis 122.

Turning to the operation of the suture retainer 200, shown in FIG. 11, FIG. 14A is a partial cross-sectional view of the assembled suture retainer 200 including a housing 210. As illustrated, opposing forces, shown as directional arrows F, have been applied to notched body 110 and opposing body 130 to compress coiled body 120 to create a gap g between the bodies for a suture 140. As the opposing forces are reduced the coiled body 120 is released, the suture retainer 200 begins to bring the notched body 110 and the opposing body 130 closer together, as illustrated in FIG. 14B. As inclined surfaces 111, 131 move toward each other, they begin to engage the suture 140, and movement of the suture 140 becomes more difficult, allowing the suture to be properly tensioned. Once the opposing forces are completely removed the coiled body 120 is fully released, the inclined surfaces 111, 131 completely engage suture 140, as shown in FIG. 14C. Once the suture is in place, adjustments to the position of the retainer 200 or tension on the suture can be achieved by holding the notched body 110 in place and partially releasing the force on the opposing body 130, or vice versa. Similarly, the notched body 110 and the opposing body 130 can be simultaneously moved with respect to each other to achieve the same result. This process can be repeated as often as desired to increase or reduce the tension on suture 140 in order to optimize the therapeutic effect.

Figure 15B:
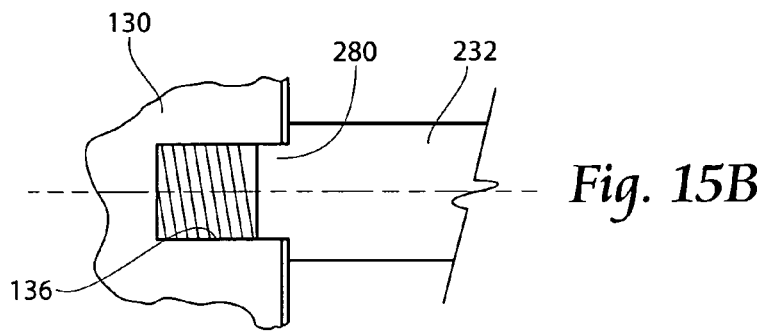
FIGS. 15A-C illustrates alternate configurations of attachment mechanisms for the suture retainers disclosed, including engagement of a control wire and catheter.
Figure 15A:
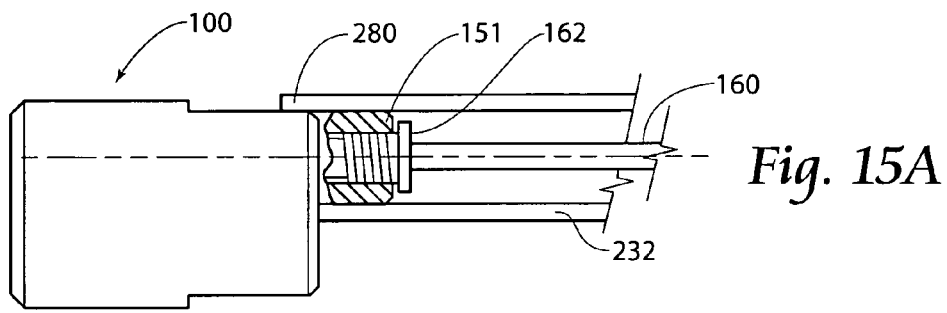
Figure 15C:
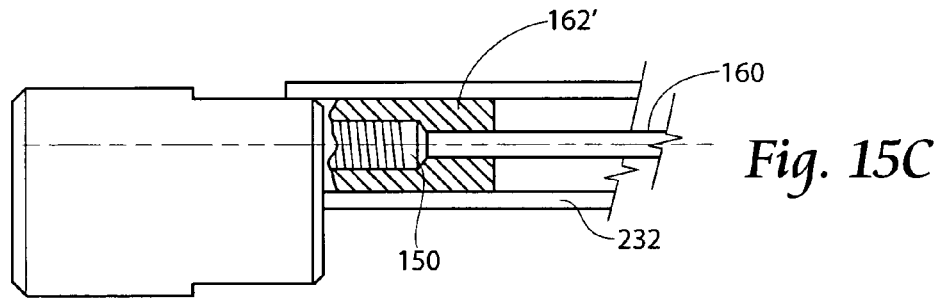

FIG. 15 illustrate alternate configurations of controlling apparatus mechanisms for the suture retainers disclosed, including engagement of the controlling elements the control wire 160 and catheter 232. FIG. 3 illustrated an attachment mechanism for the notched body 110 in the form of a threaded male member 150, onto which a control wire 160 with a threaded female member on the distal end could be attached. In lieu of the threaded male member ISO of FIG. 3, as shown in partial cutaway view FIG. 15A a female threaded aperture 151 could be provided to receive a male threaded member 162 of a control wire 160. The control wire 160 in combination with the catheter 232 enables the user to either prevent movement of the notched body 110 relative to the opposing body 130, or allows the user to control movement of the notched body 110 relative to the opposing body 130. The control wire 160 can transfer a tensile force to the notched body 110 while the catheter 232 transfers an opposing compressive force to the opposing body 130. As shown in FIG. 15B, the catheter 232 also includes a key 280 at the distal end to engage slot 136 of opposing body 130 to provide counter torsion to the mating and de-mating of the threaded connector 162 into and out of the female threaded aperture 151. In an alternative embodiment as shown in FIGS. 10-14 the key 280 can also engage one of the housing slots 214, which prevents the housing 210 from rotating when the control wire 160 is rotated to couple or uncouple with the mating member of the notched body 110. FIG. 15C illustrates an alternative controlling apparatus mechanism with a female threaded connector 162' on the end of control wire 160, engaged with a threaded male member 150.

Figure 16A:
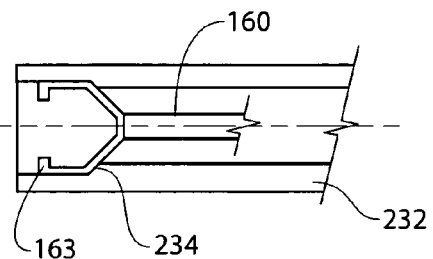
FIGS. 16A-C illustrates another alternate configuration of an attachment mechanism for the suture retainers disclosed, including engagement of a control wire and catheter.
Figure 16B:
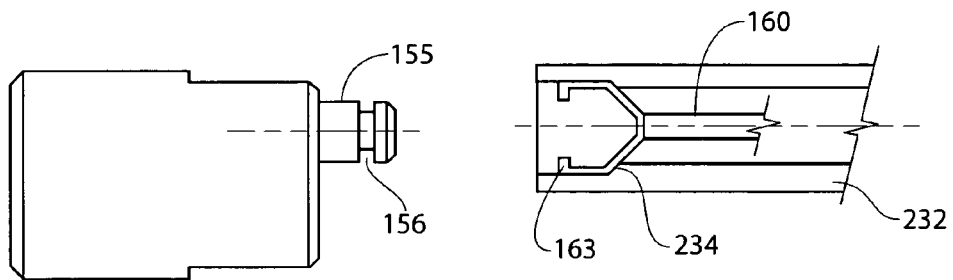
Figure 16C:
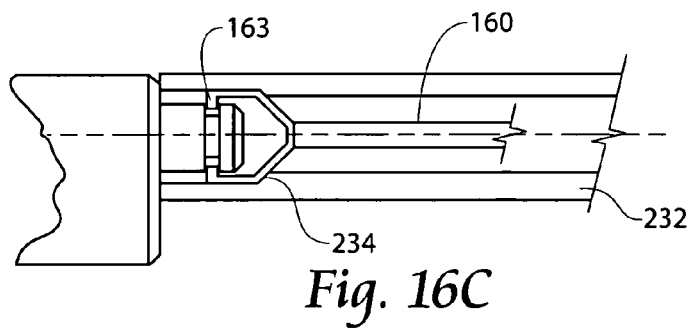

FIG. 16 illustrates another alternate control mechanism for the suture retainers disclosed, including engagement of the control mechanism. In this embodiment, the proximal end of the notched body 110 has an extension 155 with a groove 156. The control wire 160 is adapted to latch the extension 155, by engaging the groove 156 with a pair of hooks 163 extending from the end of the control wire 160. Engagement results by means of cam action when the stepped end of catheter 232 is advanced toward the retainer 100. With this embodiment, the control wire 160 could be tubular to receive the suture. The inner diameter of the catheter 232 has a step 234 that functions to provide a cam action when the hooks 156 of the control wire 160 engages the retainer 100.

Figure 17A:
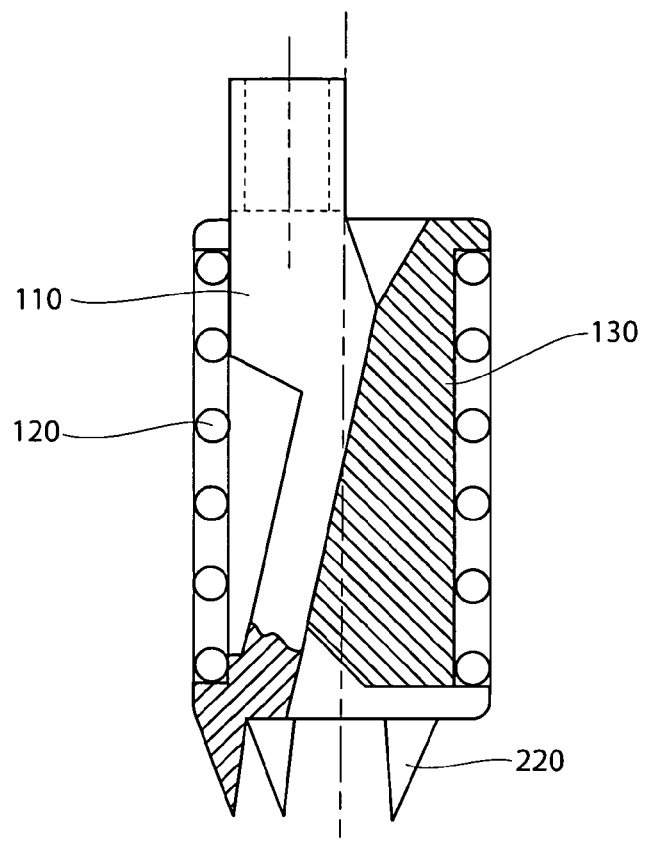
FIGS. 17A-B illustrates a partial cross-sectional view and distal view of optional spikes that can be incorporated into the suture retainer device.
Figure 17B:
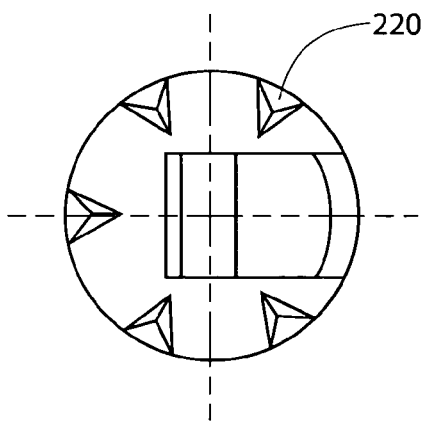

FIG. 17 illustrates in partial cross-sectional side view and distal end view, optional spikes that can extend distally from the distal flange of notched body 110. The spikes 220 are configured to enable the suture retainer to penetrate tissue or other structure and prevent the housing from rotating, or otherwise moving. Thus the spikes 220 anchor the suture retainer 200 to provide a counter-torque when unscrewing a connector, such as a control wire, from the suture retainer. Additionally, as will be appreciated by those of skill in the art, the spikes 220 can be provided in a variety of shapes or locations without departing from the scope of the invention. Thus, the spikes 220 can, for example, be provided on the distal surface of the notched body 110, or can be provided on the distal surface of the housing 210.

Figure 18A:
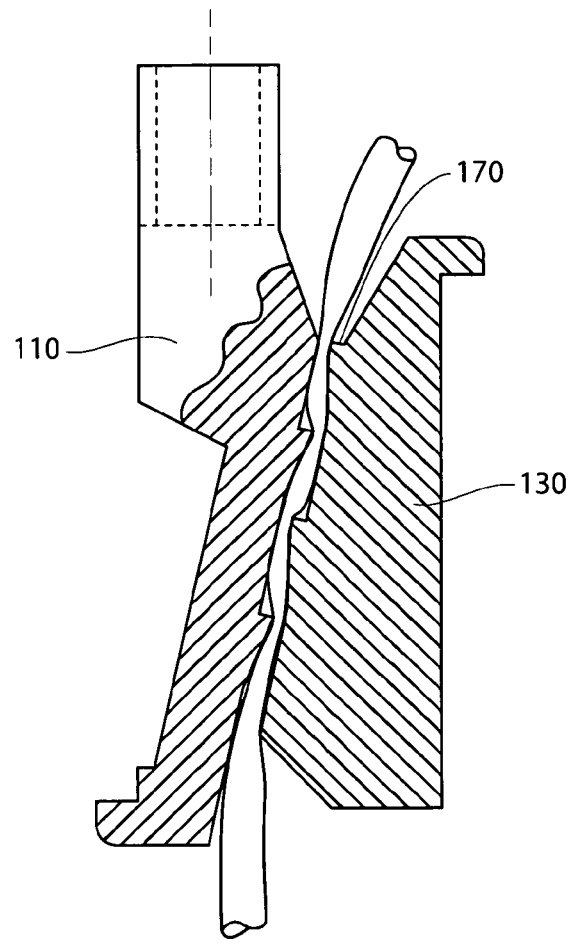
FIGS. 18A-B illustrate a partial cross-sectional view of configurations of teeth that can be provided on the surface of either or both of the notched body and the opposing body on the planar surfaces that contact the suture during operation to control the path of the suture from a proximal end of the device to a distal end of the device.
Figure 18B:
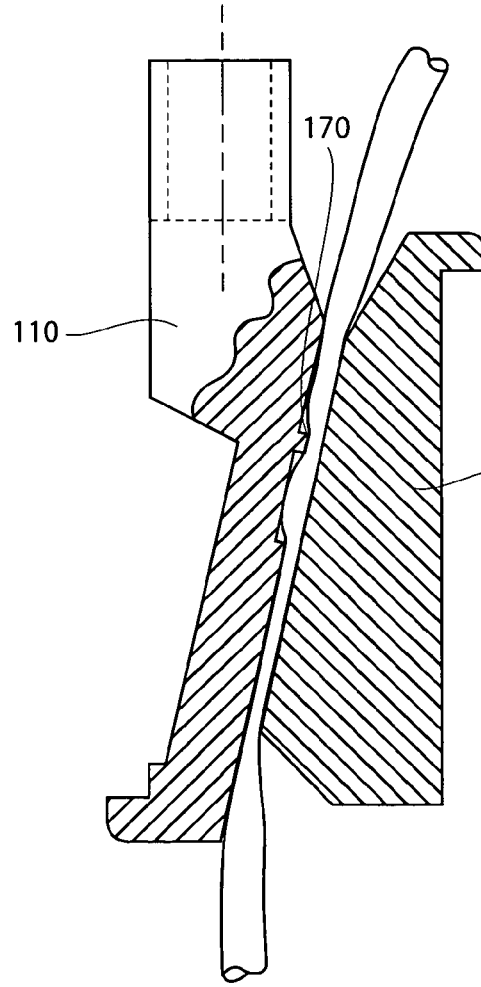

FIGS. 18A-B illustrate a side partial cross-sectional view of optional teeth 170 configurations that can be incorporated into either or both of the inclined suture contact surfaces 111 and 131 of the notched body 110 and the opposing body 130 that contact the suture 140 during operation. The teeth serve to deform the suture, increasing pull-out resistance. As will be appreciated by those of skill in the art, other configurations of teeth can be used, if desired, without departing from the scope of the invention.

Figure 19:
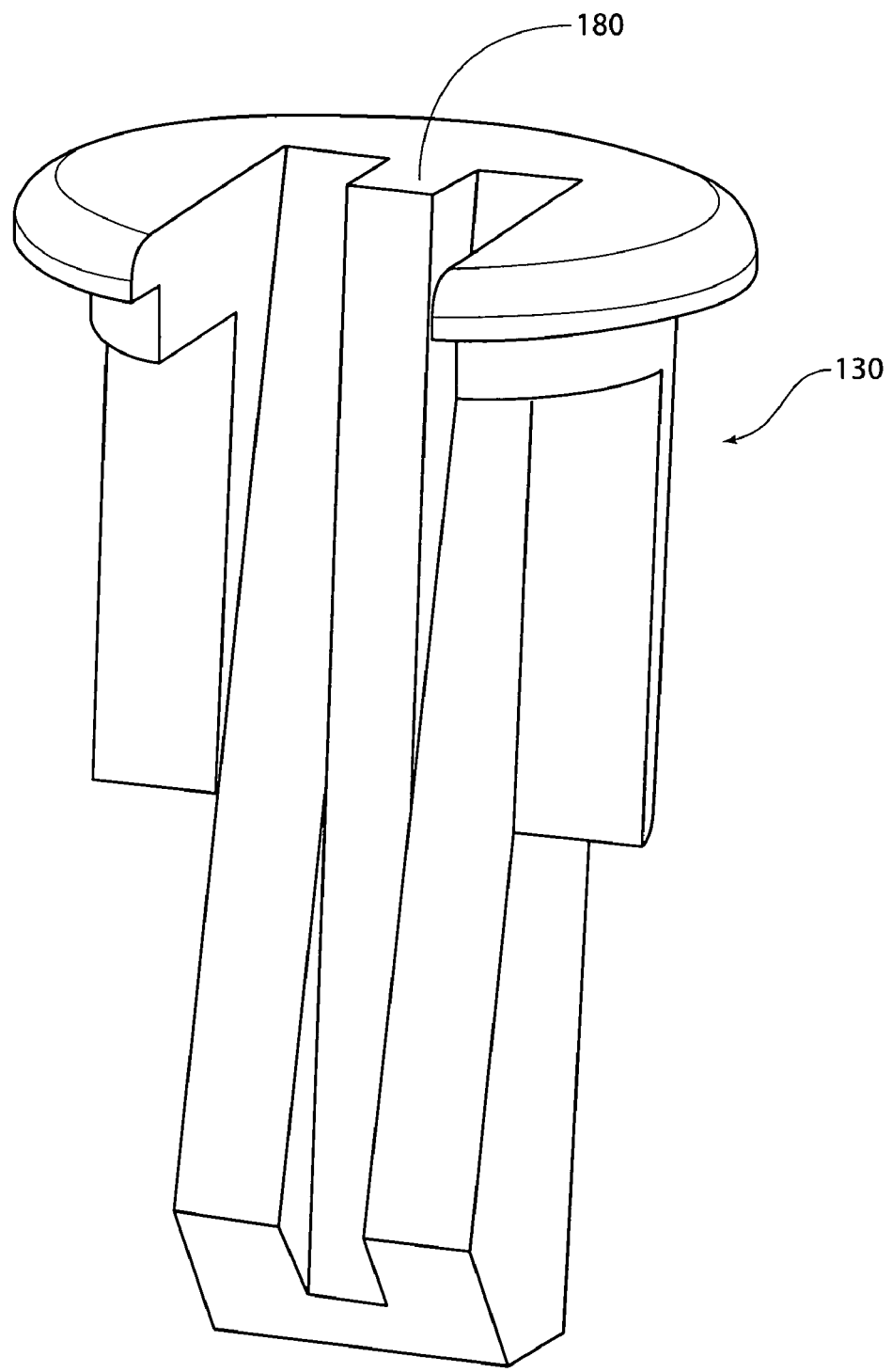
FIG. 19 is a perspective view of an alternate embodiment of an opposing body of the suture retainer having a tongue to control the path of a first suture relative to a second suture engaged by the suture retainer.

FIG. 19 is a perspective view of an alternate embodiment of an opposing body 130 of the suture retainer designed to retain two sutures, having a central ridge 180 to control the location of a first suture relative to a second suture engaged by the suture retainer. By confining multiple sutures to separate locations, the ridge 180 ensures that an approximately even retension force is imposed on both sutures by the suture retainer. As will be appreciated by those of skill in the art, where it is desirable to house more than two sutures, additional ridges can be provided, or other mechanisms, to enable the suture retainer to engage multiple sutures, while preventing the sutures from becoming crossed or tangled.

Figure 20A:
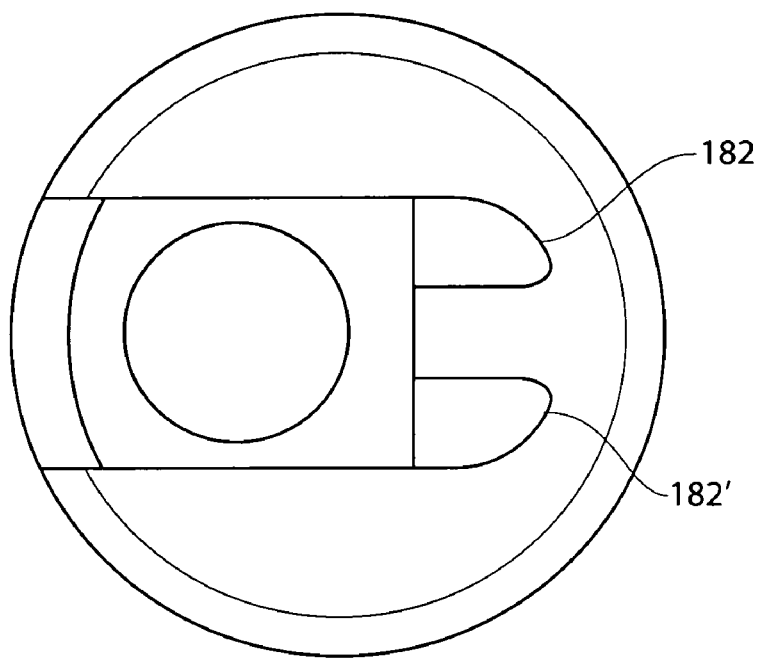
FIG. 20A illustrates a proximal view of the suture retainer shown in FIG. 19 wherein the channels for guiding the sutures are rounded.
Figure 20B:
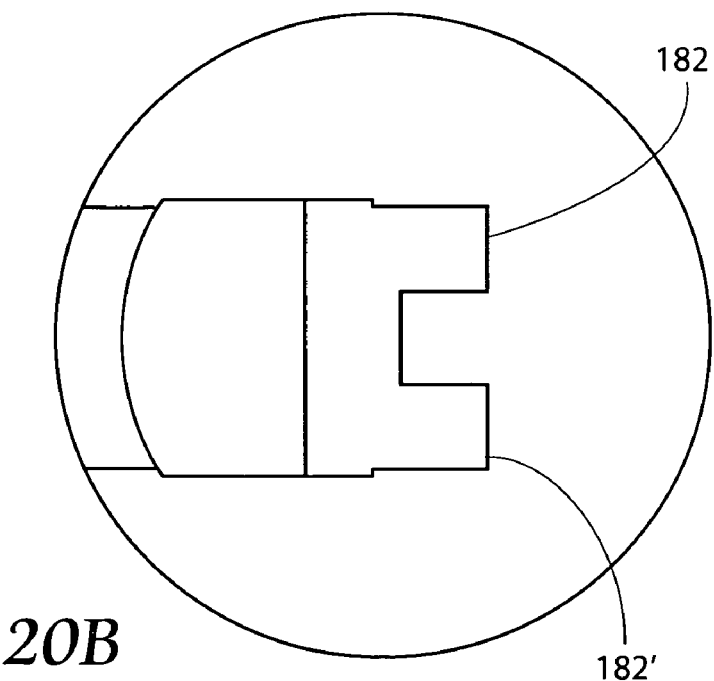
FIG. 20B illustrates a distal view of the suture retainer shown in FIG. 19 wherein the channels for guiding the sutures are rectangular.

FIG. 20A-B illustrates views of the suture retainer shown in FIG. 19 wherein the channels 182, 182' for guiding the sutures are rounded (FIG. 20A) or rectangular (FIG. 20B). Persons of skill in the art will appreciate that the channels used for the sutures can take on a variety of configurations without departing from the scope of the invention, including, for example, oval.

Figure 21A:
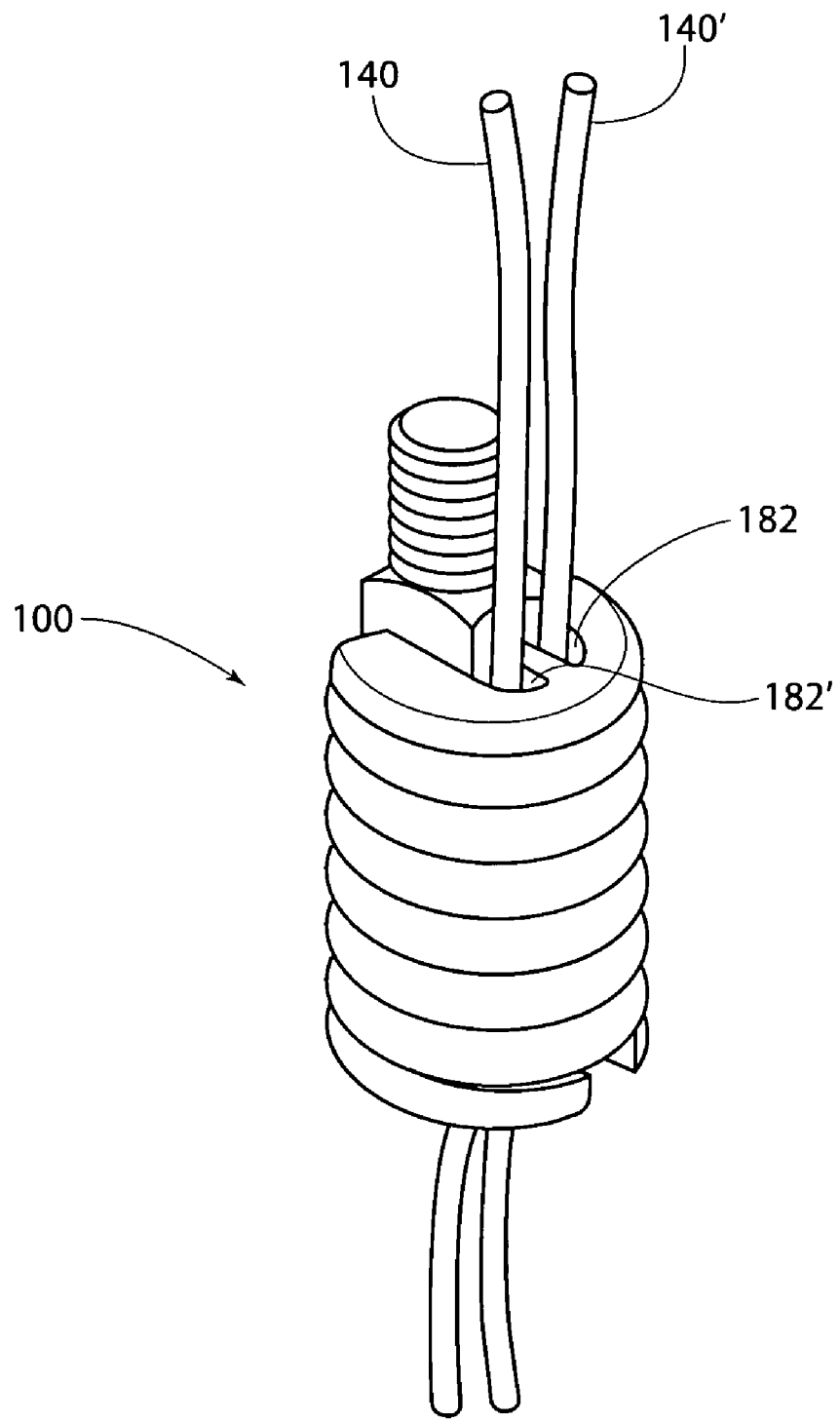
FIG. 21A is a perspective view of an embodiment of a suture retainer engaging two sutures.

FIG. 21 is a perspective view of an embodiment of a suture retainer 100' engaging two sutures 140, 140' in separate channels 182, 182'.

Figure 22A:
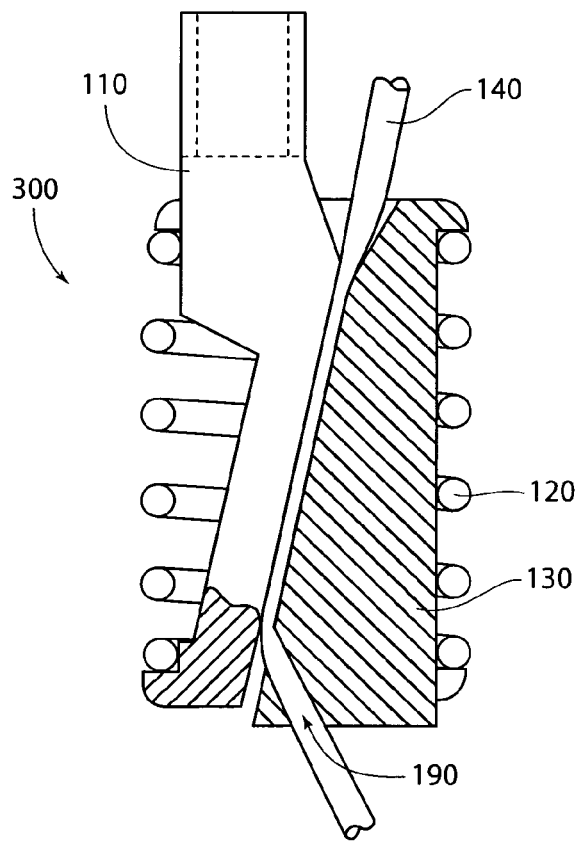
FIG. 22A-B illustrate partial cross-sectional views of embodiments of a suture retainer having alternative paths at the distal (FIG. 22A) and proximal (FIG. 22B) ends for the suture to enter or exit the device.
Figure 22B:
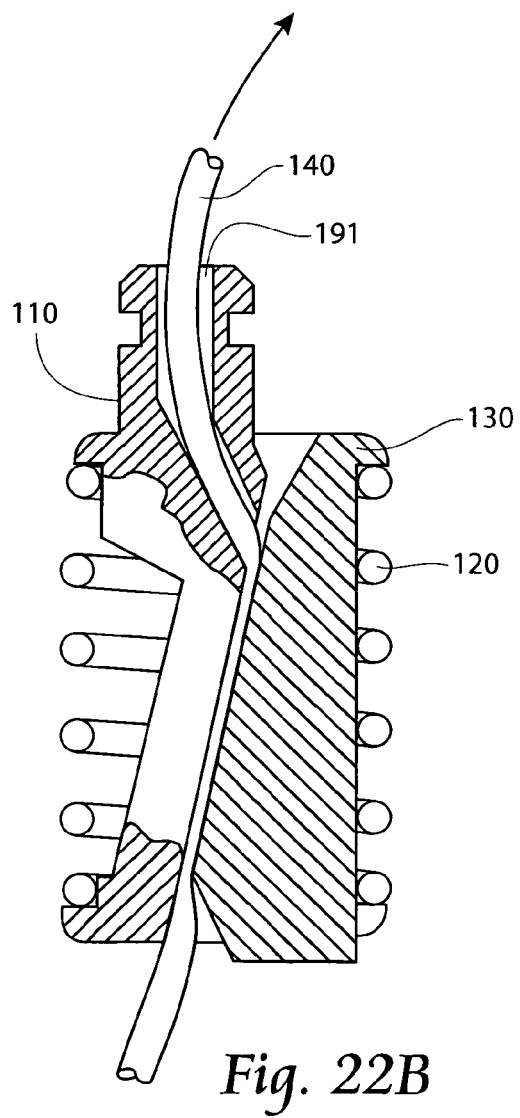

FIGS. 22A-B illustrates partial cross-sectional views of embodiments of the suture retainer having alternative paths at the distal and proximal ends of the suture retainer 300 for the suture entry into and exit from the device. In the embodiment shown in FIG. 22A, the distal end of the opposing body 130 has been provided with a hole 190 at an angle leading into the channel between contact surfaces 111, 131 as an entry for suture 140 into the suture retainer. As shown in FIG. 22B the proximal end of the notched body 110 has been provided with an exit hole 191 for the suture leading from the channel between contact surfaces 111 and 131 out through the proximal notched extension of body 110. As will be appreciated, the suture 140 can enter or exit the suture channel through any suitable lumen on the distal or proximal end of the notched body 110 or the opposing body 130 without departing from the scope of the invention. One advantage to the embodiment shown in FIG. 22B is that the location of the suture exit channel 191 co-axial with extension 155 of the notched body 110 allows use of the suture 140 as a guide for locating extension 155 with a control mechanism. Other alterations in the entry and exit path for the suture can be employed without departing from the scope of the invention.

Figure 23A:
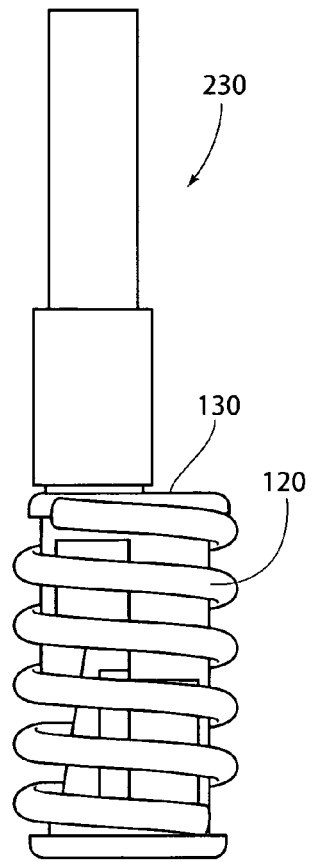
FIGS. 23A-C are views of a suture retainer with a control wire attached to the notched body (FIG. 23A); the control wire attached to the notched body within a catheter (FIG. 23B); and compression of the coiled body (FIG. 23C)
Figure 23B:
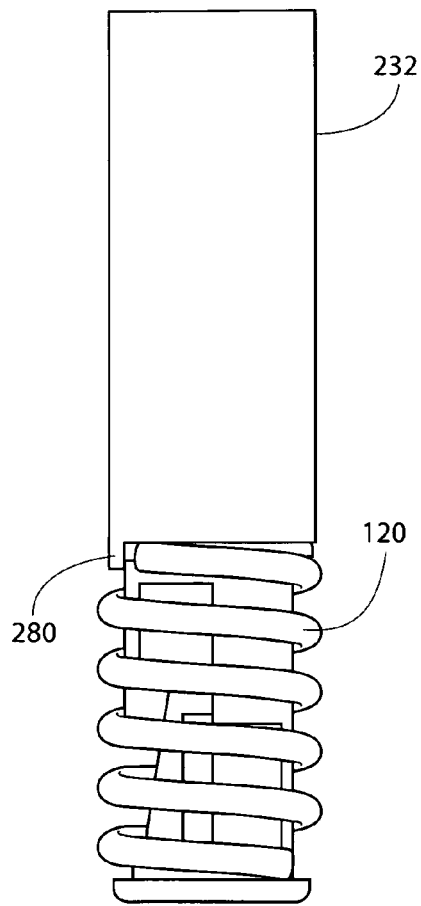
Figure 23C:
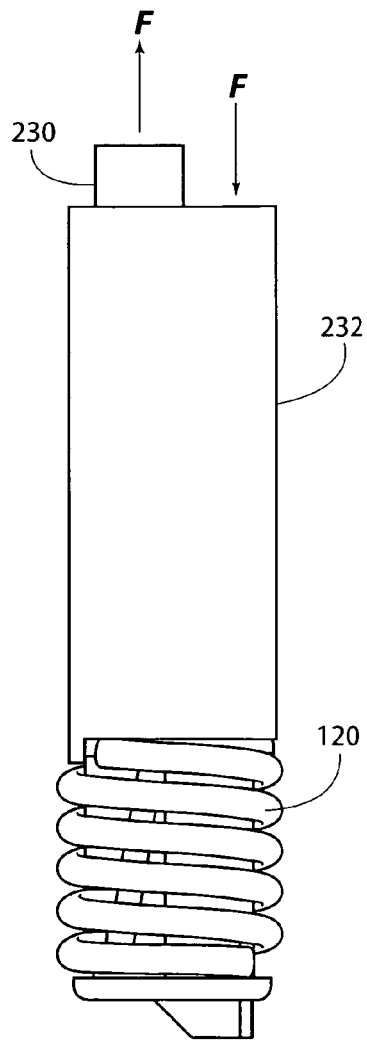
Figure 23D:
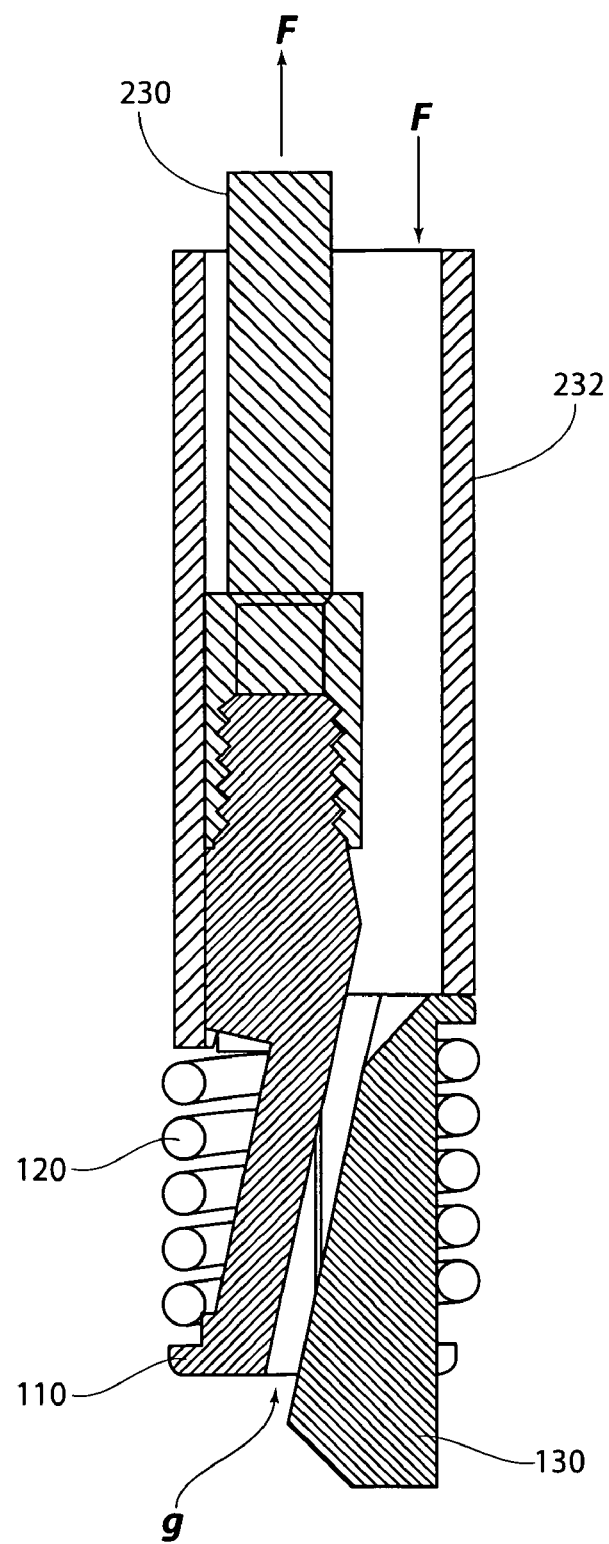
FIG. 23D is a cross-section of the assembly shown in FIG. 23C.

FIGS. 23A-C are views of a suture retainer with a connector 230 attached to the notched body 110 (FIG. 23A); the connector 230 is attached to the notched body 110 within a catheter 232 as shown in FIG. 23B. In operation, compression of the coiled body 120 as shown in FIG. 23C can occur by pulling on the connector 230 or pushing on the catheter 232, or a combination thereof. FIG. 23D illustrates a cross-section of the assembly shown in FIG. 23C wherein the notched body 110 and the opposing body 130 are separated by either pulling on the connector 230, pushing on the catheter 232 or a combination thereof which produces a gap g which is suitable for feeding a suture 140 (not shown).

Figure 24C:
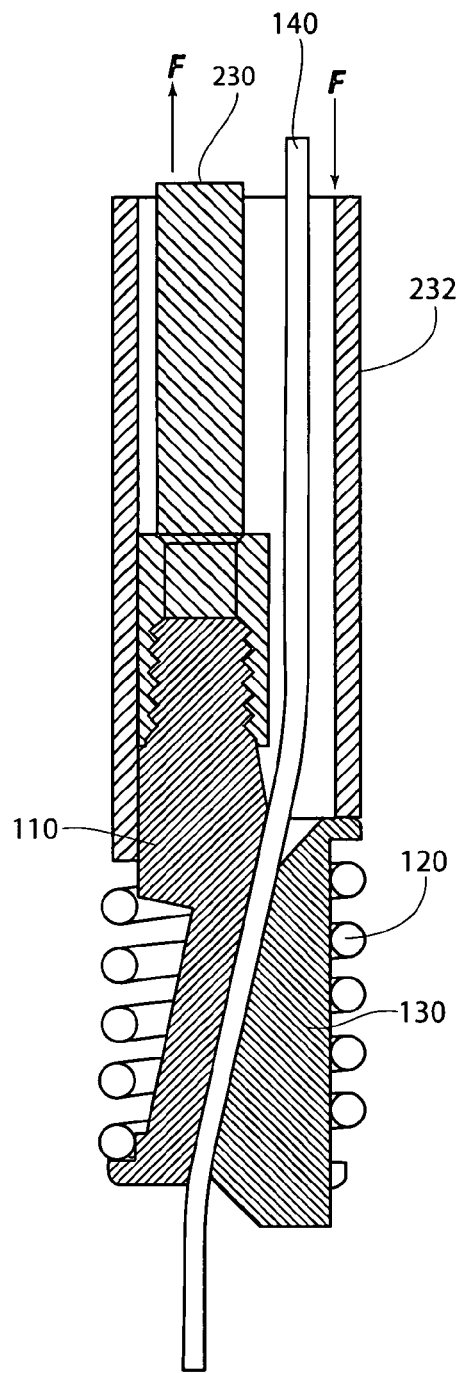
FIG. 24C is a cross-section of the retainer show in FIG. 24A showing the coiled body partially released.
Figure 24D:
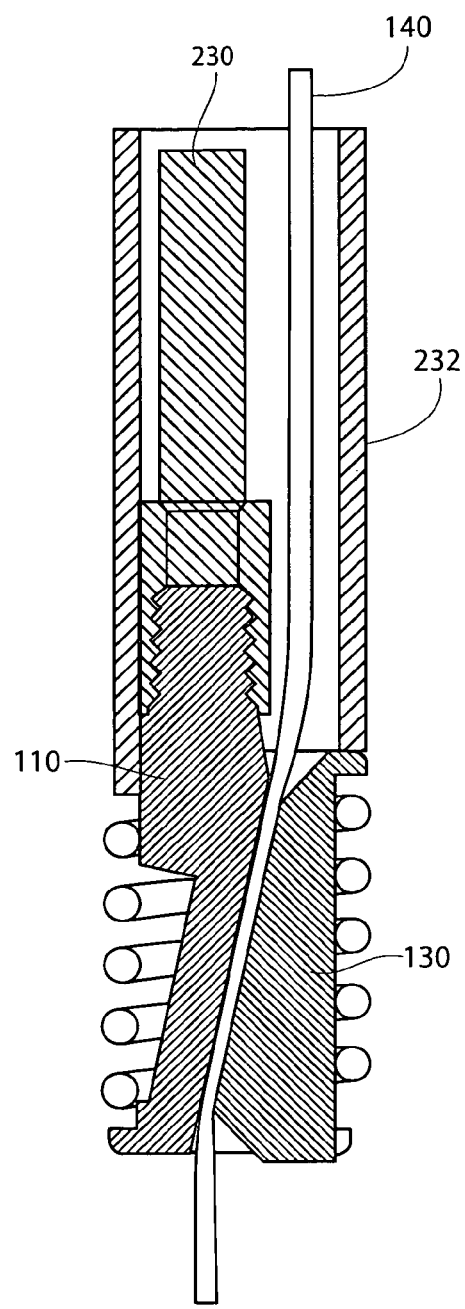
FIG. 24D is a cross-section of the retainer show in FIG. 24A showing the coiled body fully released, ready for disengagement of the catheter and control wire.

FIG. 24A illustrates a suture retainer according to the invention which is engaged with a suture 140, where the suture retainer 100 is in an open position with the coiled body 120 compressed, i.e. a gap g is present between the inclined opposing faces 111, 131 suitable to allow movement of the suture 140 therethrough. FIG. 24B illustrates a cross-section of the retainer shown in FIG. 24A showing the coiled body 120 compressed. FIG. 24C is a cross-section of the suture retainer shown in FIG. 24A showing the coiled body 120 partially compressed such that the suture 140 is retained within the suture retainer. Finally, FIG. 24D is a cross-section of the retainer shown in FIG. 24A showing the coiled body 120 released enabling the inclined opposing faces 111, 131 to apply a maximum amount of force on the suture 140.

Figure 25:
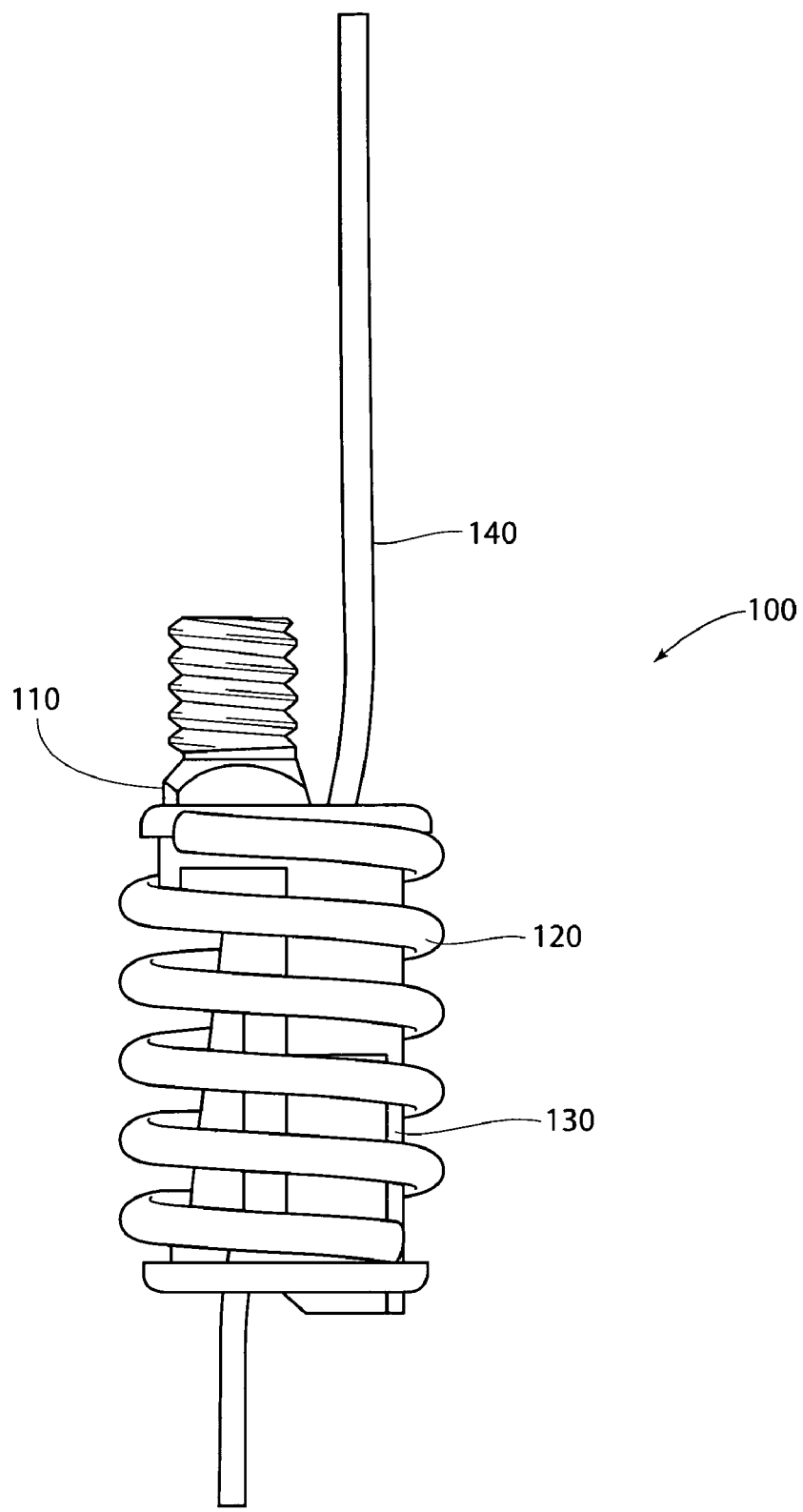
FIG. 25 illustrates a suture retainer according to the invention which has engaged a suture with the coiled body released.

FIG. 25A illustrates a suture retainer according to the invention which is engaged with a suture and the coiled body is released and control apparatus removed.

Figure 26:
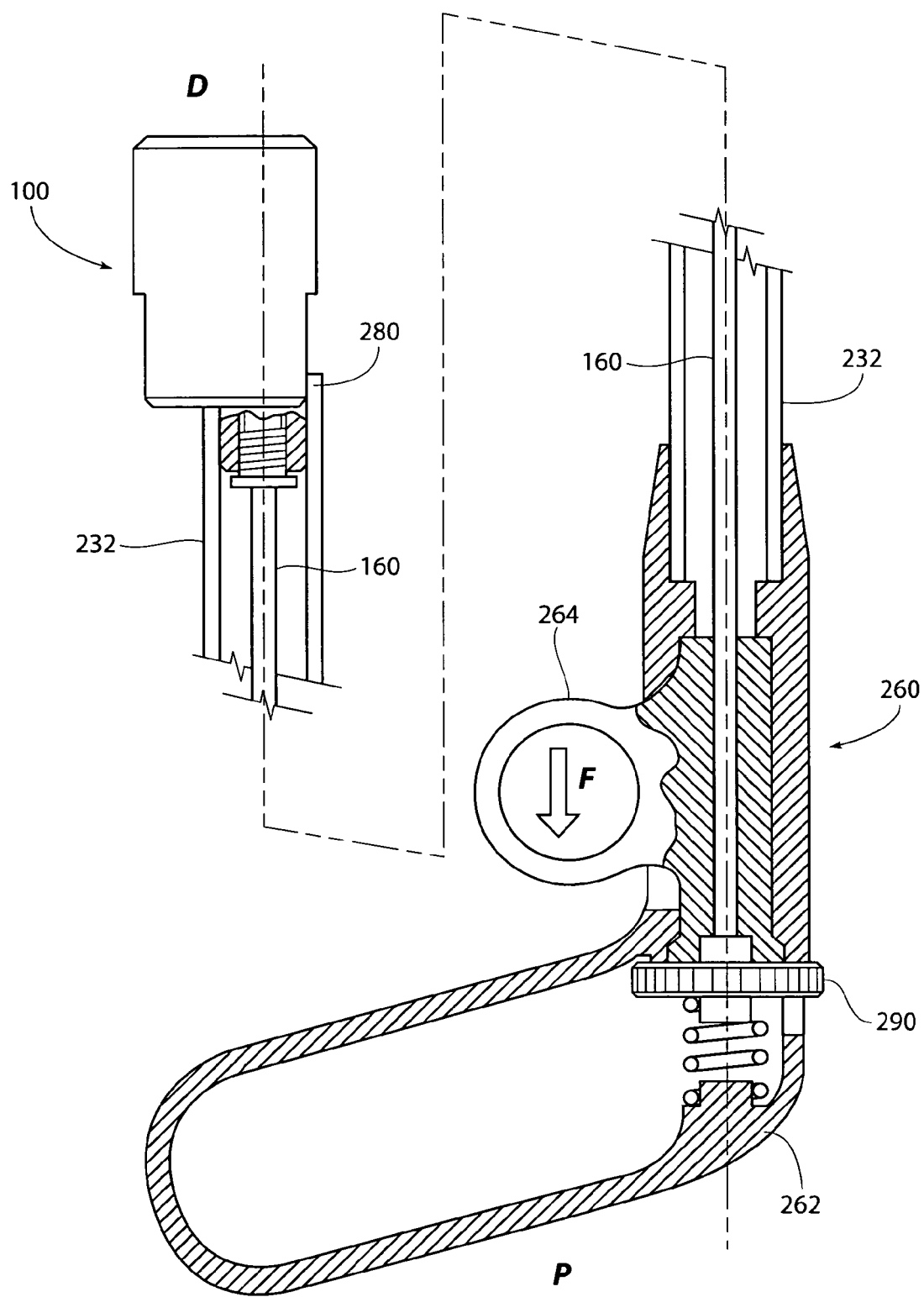
FIG. 26 illustrates a partial cross-section of a catheter and control wire apparatus with handle for use with the suture retainer of the present invention.

FIG. 26 illustrates a partial cross-section of a control apparatus 260 for use with the suture retainer of the present invention. The apparatus has a handle 262 with an actuator 264 and thumb wheel 290 at its proximal end. Revolving thumb wheel 290 revolves control wire 160 to connect or disconnect the control wire connector 160 to and from the threaded extension on the notched body 110. Revolving handle 262 relative to the suture retainer 100 will engage the catheter key 280 on the distal end of the catheter 232 into opposing body channel 136 (shown in FIG. 2). Pulling force F on the actuator 264 pulls the control wire 160 and its connector toward the user and causes the distal end of catheter 232 to push on the proximal face of opposing body 130. This compresses spring 120, creating gap g between contact surfaces 111 and 131 of the suture retainer. Releasing the trigger results in the coiled body 120 being released and the inclined opposing faces 111, 131 coming together to apply a maximum amount of force on the suture 140. It will be appreciated by those of skill in the art that many other configurations of control apparatus are possible for connecting to the suture retainer and generating opposing forces to create and control the amount of gap between contact surfaces 111 and 131 without departing from the scope of the present invention.

Figure 27:
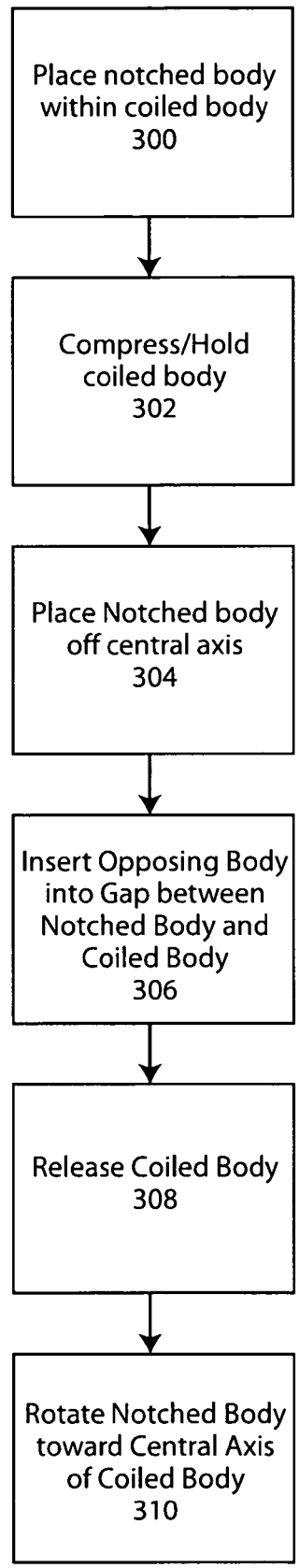
FIG. 27 is a flow chart of the steps for assembling a suture retainer according to the invention.

The process for assembling a suture retainer (without housing) of the invention is illustrated in FIG. 27. As described above, the first step 300 is to place the notched body 110 within a coiled body 120. Next, the coiled body 120 is compressed 302 and held in a compressed state. The notched body is then rotated away from the central axis 304 to create a space between notched body 110 and coiled body 120 for opposing body 130. The opposing body is then inserted into the space 306. Thereafter, the coiled body 120 is released 308, and the notched body 110 is rotated toward the central axis of the coiled body 310. As will be appreciated by those of skill in the art, the assembly process for a retainer having a housing is similar to the assembly process of the retainer without a housing.

Figure 28:
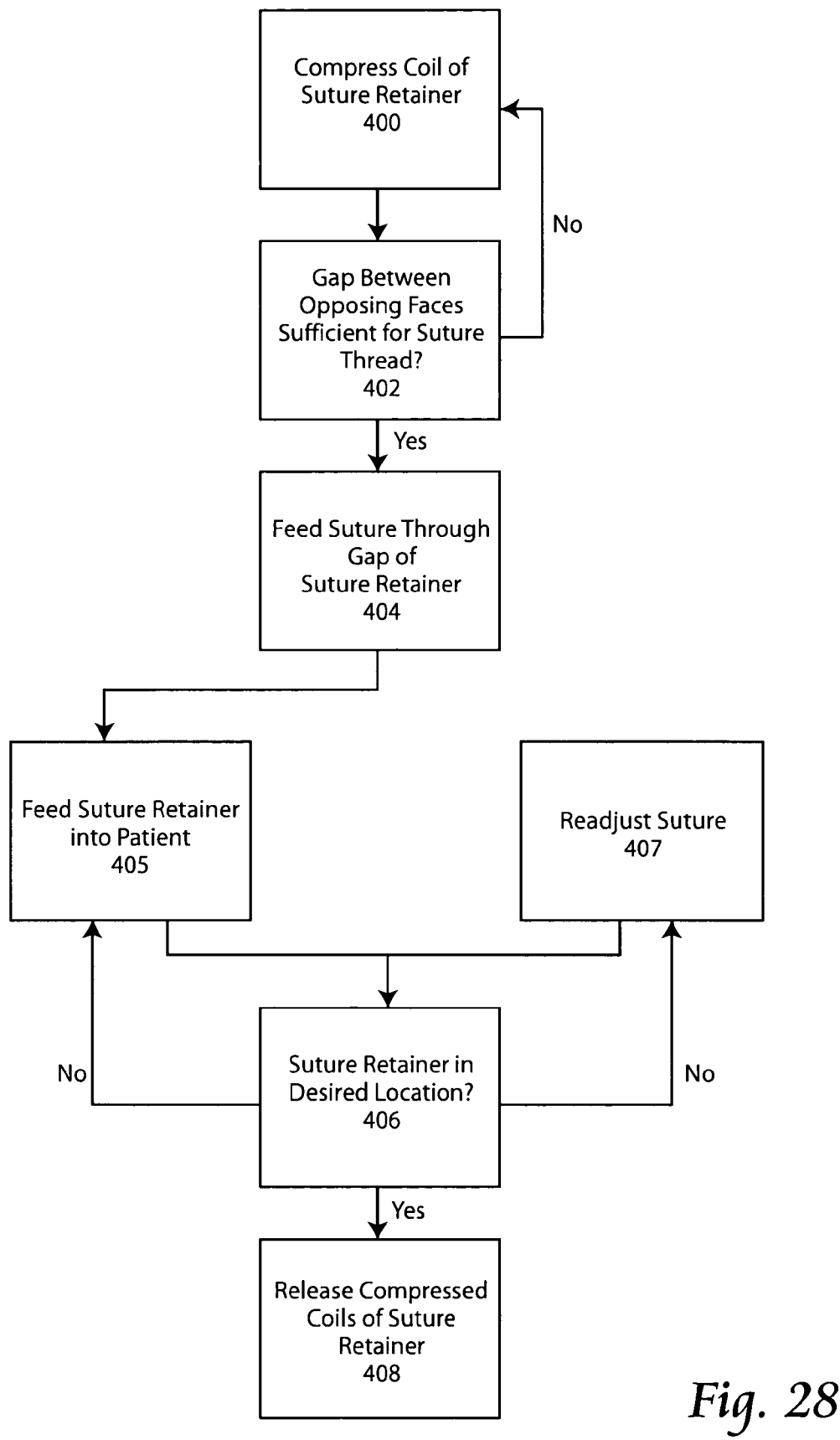
FIG. 28 is a flow chart of the steps for using the suture retainer according to the invention.

The process for using the suture retainer of the invention is illustrated in FIG. 28. The coils of the coiled body 120 of the assembled suture retainer are compressed 400 by application of opposed forces to notched body 110 and opposing body 130. As a result a gap is created between the opposing inclined faces 402. If the gap is not sufficient to feed a suture through the gap, the coils are further compressed until a sufficient gap exists. Once the gap is sufficient to feed a suture through the retainer, the suture is fed through the gap 404. The suture retainer is then moved along the suture 405 until it is positioned in a desired location. The suture retainer can be fed into the patient 405 and the suture can be readjusted 407 in the suture retainer as often as necessary to achieve desired tension and desired location. Once the suture is properly positioned 406 and tensioned, the compressive forces on the coils are released 408 and the suture retainer is locked in place. It can be appreciated by those skilled in the art that the suture retainer of the present invention can be used to retain a wide variety of sizes of suture. For example USP suture size 10 to 12-0 can be retained simply by varying the size of the gap g to thread the size suture desired.

The designs and operation of the suture retainer described herein can be incorporated into or combined with other apparatus as an elemental part or parts without departing from the spirit of this invention, or can be applied to retainers used for other applications as well. For example, larger retainers can be manufactured for retaining, thread, wire, filament, rope, twine, lanyard, cable, etc. The size and materials used to manufacture the retainer may change, but the design and principles of operation disclosed herein remain the same.

What is claimed is:

1. A suture retainer comprising:
   a unitary first retainer body member extending from a first proximal end to a first distal end, the first retainer body member comprising:
      a first flange forming a majority of the first distal end;
      a first channel formed through the first flange; and
      a first suture contact surface extending proximally from the first channel;
   a unitary second retainer body member extending from a second proximal end to a second distal end the second retainer body member comprising:
      a second flange forming a majority of the second proximal end;
      a second channel formed through the second flange; and
      a second suture contact surface extending distally from the second channel, wherein the first suture contact surface and the second suture contact surface define a suture contact axis; and a unitary coiled biasing member surrounding at least a majority of the first and second suture contact surfaces and extending between the first flange and the second flange, the coiled biasing member being adapted to bias the first and second contact surfaces toward each other, wherein the first proximal end is slidably disposed in the second channel and the second distal end is slidably disposed in the first channel, and further wherein the suture retainer has a first position in which the suture contact surfaces are at a first distance from each other and a second position in which the suture contact surfaces are at a second distance from each other, the suture retainer being adapted to retain a suture between the first and second suture contact surfaces when in the first position, the first and second channels forming a movement guide permitting relative movement between the first and second contact surfaces along a movement axis not perpendicular to the suture contact axis.

2. The suture retainer of claim 1 wherein the coiled biasing member is formed about an axis situated unorthoganally to the suture contact axis.

3. The suture retainer of claim 1 further comprising a housing in which the first and second body members are disposed.

4. The suture retainer of claim 1 further comprising a housing surrounding the coiled biasing member.

5. The suture retainer of claim 1 wherein the coiled biasing member is adapted to be moved to a position permitting rotational movement between the first and second body members.

6. The suture retainer of claim 5 wherein the coiled biasing member is adapted to be moved to a position permitting rotational movement between the first and second body members to permit assembly or disassembly of the suture retainer.

7. The suture retainer of claim 6 wherein the first body member comprises a notch further permitting rotational movement between the first and second body members.

8. The suture retainer of claim 1 further comprising a threaded tool engagement member extending from the proximal end of the first retainer body member.

9. The suture retainer of claim 8 further including a second tool engagement surface provided on the second proximal end adapted to engage a second tool with the second retainer body member.

10. The suture retainer of claim 1 further comprising a protuberance extending from the first contact surface.

11. The suture retainer of claim 10 wherein the protuberance comprises a tooth.

12. The suture retainer of claim 1 further comprising third and fourth substantially parallel suture contact surfaces defining a second suture contact axis, the third and fourth suture contact surfaces being at a first distance from each other to retain a suture when the suture retainer is in the first position and at a second distance from each other when the suture retainer is in the second position.

13. The suture retainer of claim 12 further comprising a ridge separating the first and third suture contact surfaces.

14. A suture retainer according to claim 1, wherein the first suture contact surface and the second suture contact surface are substantially planar.

* * * * *